(12) United States Patent
Yoon et al.

(10) Patent No.: US 7,871,774 B2
(45) Date of Patent: Jan. 18, 2011

(54) MARKERS FOR THE DIAGNOSIS OF LUNG CANCER

(75) Inventors: Jeong Ho Yoon, Seoul (KR); Se Nyun Kim, Seoul (KR); Jong Ho Park, Seoul (KR); Ja Eun Kim, Yongin-si (KR); Young-Hwa Song, Goyang-si (KR); Sung Han Kim, Buchcon-si (KR); Dong Yoon Park, Seoul (KR)

(73) Assignee: Digital Genomics Inc., Seoul (KR)

( * ) Notice: Subject to any disclaimer, the term of this patent is extended or adjusted under 35 U.S.C. 154(b) by 562 days.

(21) Appl. No.: 11/815,198

(22) PCT Filed: Jan. 31, 2005

(86) PCT No.: PCT/KR2005/000279

§ 371 (c)(1),
(2), (4) Date: Oct. 26, 2007

(87) PCT Pub. No.: WO2006/080597

PCT Pub. Date: Aug. 3, 2006

(65) Prior Publication Data

US 2010/0047771 A1     Feb. 25, 2010

(51) Int. Cl.
*C12Q 1/68* (2006.01)
(52) U.S. Cl. ......................................................... 435/6
(58) Field of Classification Search ........................ None
See application file for complete search history.

(56) References Cited

U.S. PATENT DOCUMENTS 6,531,315 B1 * 3/2003 Wang et al. .............. 435/372.3

FOREIGN PATENT DOCUMENTS

| | | |
|---|---|---|
| JP | 2004-163388 | 6/2004 |
| JP | 2004-518437 | 6/2004 |
| KR | 2003-0078803 A | 10/2003 |

OTHER PUBLICATIONS

Oguri et al (Int J Cancer, 2000, 86:95-100).*
Tockman et al (Cancer Res., 1992, 52:2711s-2718s).*
Wang et al (Oncogene, 2000, 19: 1519-1528).*
Hibi et al., Am. J. Pathol. 1999, 155: 711-715.
Brechot et al. Eur. J. Cancer 1997, 33: 385-391.
Morita et al., Int. J. Cancer 1998 78: 286-292.
Kohler and Milstein (1976) European Journal of Immunology 6:511-519.
Clackson et al., Nature, 352: 624-628, 1991.
Marks et al, J. Mol.Biol., 222:581-597, 1991.
Li, H,X, et al, Serum thymidine kinase 1 is a prognostic and monitoring factor in patients with non-small cell lung cancer' In: Oncol Rep, Jan. 2005, vol. 13(1) pp. 145-149.
Ouyang, Q.C., et al. 'Gene expression of MMP1 and TIMP1 in lung cancer detected with a cDNA microarray technique'In: Hunan Yi Ke Da Xue Xue Bao, Jun. 2003, vol. 28(3), pp. 227-228.
Yoshida, M., et al. 'induction of:MRP5 and SMRP mRNA by adriamycin exposure and its overexpression in human lung cancer cells resistant to adriamycin' In: Int. J. Cancer; Nov. 1, 2001, vol .94(3), pp. 432-437.

* cited by examiner

*Primary Examiner*—Sean E Aeder
(74) *Attorney, Agent, or Firm*—JHK Law; Joseph Hyosuk Kim

(57) ABSTRACT

Disclosed is a diagnostic marker specific for lung cancer. Also, the present invention relates to a composition and a kit, comprising an agent measuring the presence of the marker, and a method of diagnosing lung cancer using the composition or kit.

2 Claims, 2 Drawing Sheets

- Normal
- Tumor

SEQUENCE LISTING

```
<160> NUMBER OF SEQ ID NOS: 30

<210> SEQ ID NO 1
<211> LENGTH: 5451
<212> TYPE: DNA
<213> ORGANISM: Homo sapiens

<400> SEQUENCE: 1
gggtggtgca gggcaggggt ggtatatcct gtctgacgga gggcgggcct cgccagtgcc      60
agagagggac gaaccagggt ggaagcgcca ggagcagctg cagggagccc tcacgcggac     120
ctcgcactct atggccgtag ggagccgctg agagcgagaa gagcacgctc ctgcccgccc     180
gctgcaccgc acctcgcctc gcctctctgc tctcctaggc cccggccgcg cgccacccgc     240
ctcccgccac catgaaccac tcgccgctca agaccgcctt ggcgtacgaa tgcttccagg     300
accaggacaa ctccacgttg gctttgccgt cggaccaaaa gatgaaaaca ggcacgtctg     360
gcaggcagcg cgtgcaggag caggtgatga tgaccgtcaa gcggcagaag tccaagtctt     420
cccagtcgtc caccctgagc cactccaatc gaggttccat gtatgatggc ttggctgaca     480
attacaacta tgggaccacc agcaggagca gctactactc caagttccag gcagggaatg     540
gctcatgggg atatccgatc tacaatggaa ccctcaagcg ggagcctgac aacaggcgct     600
tcagctccta cagccagatg gagaactgga gccggcacta ccccggggc agctgtaaca     660 ccaccggcgc aggcagcgac atctgcttca tgcagaaaat caaggcgagc cgcagtgagc     720
ccgacctcta ctgtgaccca cggggcaccc tgcgcaaggg cacgctgggc agcaagggcc     780
agaagaccac ccagaaccgc tacagctttt acagcacctg cagtggtcag aaggccataa     840
```

-continued

```
agaagtgccc tgtgcgcccg ccctcttgtg cctccaagca ggaccctgtg tatatcccgc      900
ccatctcctg caacaaggac ctgtcctttg ccactctag  ggccagctcc aagatctgca      960
gtgaggacat cgagtgcagt gggctgacca tccccaaggc tgtgcagtac ctgagctccc     1020
aggatgagaa gtaccaggcc attggggcct attacatcca gcatacctgc ttccaggatg     1080
aatctgccaa gcaacaggtc tatcagctgg gaggcatctg caagctggtg gacctcctcc     1140
gcagccccaa ccagaacgtc cagcaggccg cggcaggggc cctgcgcaac ctggtgttca     1200
ggagcaccac caacaagctg gagacccgga ggcagaatgg gatccgcgag gcagtcagcc     1260
tcctgaggag aaccgggaac gccgagatcc agaagcagct gactgggctg ctctggaacc     1320
tgtcttccac tgacgagctg aaggaggaac tcattgccga cgccctgcct gttctggccg     1380
accgcgtcat cattcccttc tctggctggt gcgatggcaa tagcaacatg tcccgggaag     1440
tggtggaccc tgaggtcttc ttcaatgcca caggctgctt gagaaagaga ctgggcatgc     1500
gggagcttct ggctcttgtt ccgcaaaggg ccactagtag cagggtgaac ctgagctcgg     1560
ccgatgcagg ccgccagacc atgcgtaact actcagggct cattgattcc ctcatggcct     1620
atgtccagaa ctgtgtagcg ccagccgct  gtgacgacaa gtctgtggaa aactgcatgt     1680
gtgttctgca aacctctcc  taccgcctgg acgccgaggt gcccaccgc  taccgccagc     1740
tggagtataa cgcccgcaac gcctacaccg agaagtcctc cactggctgc ttcagcaaca     1800
agagcgacaa gatgatgaac aacaactatg actgcccct  gcctgaggaa gagaccaacc     1860
ccaagggcag cggctggttg taccattcag atgccatccg cacctacctg aacctcatgg     1920
gcaagagcaa gaaagatgct accctggagg cctgtgctgg tgccctgcag aacctgacag     1980
ccagcaaggg gctgatgtcc agtggcatga gccagttgat tgggctgaag gaaaagggcc     2040
tgccacaaat tgcccgcctc ctgcaatctg gcaactctga tgtggtgcgg tccggagcct     2100
ccctcctgag caacatgtcc cgccaccctc tgctgcacag agtgatgggg aaccaggtgt     2160
tcccggaggt gaccaggctc ctcaccagcc acactggcaa taccagcaac tccgaagaca     2220
tcttgtcctc ggcctgctac actgtgagga acctgatggc ctcgcagcca caactggcca     2280
agcagtactt ctccagcagc atgctcaaca acatcatcaa cctgtgccga agcagtgcct     2340
cacccaaggc cgcagaagct gcccggcttc tcctgtctga catgtggtcc agcaaggaac     2400
tgcagggtgt cctcagacag caaggttccg ataggaacat gctgggaacc ttagctgggg     2460
ccaacagcct caggaacttc acctcccgat tctaagaaga gactgtccaa gcaagttagg     2520
cttgcaggaa gatatgaccc agctgagaag ccctcaggcc tcgctggatg gggttttctg     2580
tccatcctat gcagtatttg gaaagttcaa caagaaactg agaagaaacc taaaaactgt     2640
ggatagtgga aagatttta  gatttttttt ttccttgggg aaactggcag gcaatgggg      2700
ttagggaggt tggggcggtg ggggcttttct tgagttaaag gggcttatat gtgatgtcaa     2760
tatttcttcc tctgagaaat ggtatatata tgtgtataat gtaagtgtgt gcatgcatgt     2820
gcgcgtgcat gtgtgtgtgt gtgagtgtct taaagcataa ccacaaactg caaaaagcta     2880
ggtaagctat tttgttgcag ctcataaggt ggtgaaaagg actctcctgt gtttcttact     2940
cataggcaag gacaacatgt gcttttggt  gagctgctca taattcctga aatgtgtggt     3000
gccagggcaa gggggccatc actgcagtca ggccctcaga ggagtcctgc aggcttccta     3060
ccagtggtct ccaggggtgc aggagtaact ggggctgggc cagcctcccc acttacaagg     3120
ctgcttttcca ggaagggagg tctggtgtat ctcatgggag aatctggggt gtctgtaatg     3180
```

-continued

```
tcacccctcc agcagcgcca caaggactga ggttgggtag gtgtggggtt ccagaggaca    3240
gcaggacact ctcgcatact ttgccaaatg aggcctgctc agaggagtag gagctgaaag    3300
atggtgcctt ccaccctctt gggctgtgtg cccatcagag caggctcagc ctgcaaaggc    3360
cctgcattca gaggtcttgt aatctacttg ttgcaggaga aagaaggtaa aaaatgattt    3420 tttttaagaaa agctatttta ttgcagctct ttcccaagag ctgttctggg aatggctggt    3480
cttcatattc ccagtggaga ggggaacaag tggggctggg catataccta ttccggcttc    3540
tagtgggatg gagttggggt atagaaatta accaggaaga tgtttccacc aagcctgctg    3600
tgagtcaatt gagggagtgt ttggggtccc aggagacttg gacgggggga gtttgggtag    3660
actaggaaag gaaagtgcca tatcagggta ccggtaccgg caagctcaca tctcagccag    3720
gggccatgcc ccacttcccc tgaccccagc tgtcttgtct ccactctgtg aaacccacag    3780
gggatgtgat aaacagggct attaggggta tcagccacgt cgagccccca gactctgtgc    3840
acttcagacc agcagcagca ggagggctcc cgagggcctt atgagaaaac ctgtgtggac    3900
atcccttggt gtacactaag acagagcaga gcccagcgct cccaagcctt cctccttcca    3960
gcttctacct ccatgctagc attgctggtg ttagagagga attaacttcc tggtctgtgc    4020
ccttctctag aagaatataa gatgctcctc ctcctcaccc cttctcagcc tcctcccaag    4080
tcttcctctt ctgcaccacc cccgagtcca aacccacctc ttgccccagc attcaggctg    4140
gaaaacactg atgtggactc agtatgataa ctgagatggg ggacgccaga catgtgagga    4200
cgctgtcctc cgagaggtgt ccccggctgt tagccagctg tgctgtggtg ctgtgggtct    4260
gtcataccct cccttgcttc tgttcacact gggaggccca ctcctggctc acctctccct    4320
ctcagggacc cacgtgggag cctggatccc tggactgtcc tgggcatagg tttcaggggc    4380
ctcctttgtt gtcatcagaa cccagaggaa ttcttctcct aaaaaatacg tatggcatac    4440
caatctgtgc ggggcagtgt cctaagcact tagactacat cagggaagaa cacagaccac    4500
atccctgtcc tcatgcggct tatgttttct ggaggaaagt ggagacacaa gtccttggct    4560
ttagggctcc cccggctggg ggctgtgcag tccggtcagg gcgggagggg aaatgcaccg    4620
ctgcatgtga accttaccag cccaggcgga tgccccttcc ccttagcact accctggcct    4680
cctgcatccc ctcgcctcat gttcctccca ccttcaaaga atgaagagcc ccatgggccc    4740
agcccctgcc ctgggaacca ggcagccttc cagacctcag gggctgaggc agactattag    4800
ggcagggctg actttggtga cactgcccat tccctctcag gccagctcag gtcacccggg    4860
cctctgaccc aggcctgtca ctttgagagg ggcaaaactg agaggggctt ttcctagaga    4920
aagagaacaa ggagcttgcc aggcttcatg tagccgacac acgtctcagg attttaagtc    4980
cacattggcc tcacactacc agggccaatg cccaaaataa ggagttccaa tttggggcca    5040
aatgaggaag gacacagact ctgccctggg atctcctgtg ctagcggcca atgacaaatc    5100
cagtcattgg ccaccagcca cctctgcagt ggggaccaca ctagcagccc tgactccaca    5160
ctcctcctgg ggacccaaga ggcagtgttg ctgtctgcat gtccaccttg aatctggct    5220 gaactggctg caggaccaa gactgcggct ggggtgggca gggaagggaa gccggggct    5280 gctgtgaggg atcttggagc ttccctgtag cccaccttcc ccttgcttca tgtttgtaga    5340
ggaaccttgt gccggccagg cccagtttcc ttgtgtgata cactaatgta tttgcttttt    5400
ttggaaatag agaaaatcaa taaattgcta gtgtttcttt gaaaaaaaaa a             5451
```

<210> SEQ ID NO 2
<211> LENGTH: 18

```
<212> TYPE: DNA
<213> ORGANISM: Artificial
<220> FEATURE:
<223> OTHER INFORMATION: primer for amplification of PKP1

<400> SEQUENCE: 2
agtggcatga gccagttg                                                  18

<210> SEQ ID NO 3
<211> LENGTH: 20
<212> TYPE: DNA
<213> ORGANISM: Artificial
<220> FEATURE:
<223> OTHER INFORMATION: primer for amplification of PKP1

<400> SEQUENCE: 3
ctggttcccc atcactctgt                                                20

<210> SEQ ID NO 4
<211> LENGTH: 5838
<212> TYPE: DNA
<213> ORGANISM: Homo sapiens

<400> SEQUENCE: 4
ccgggcaggt ggctcatgct cgggagcgtg gttgagcggc tggcgcggtt gtcctggagc     60
aggggcgcag gaattctgat gtgaaactaa cagtctgtga gccctggaac ctccgctcag    120
agaagatgaa ggtatcgac ataggaaaag agtatatcat ccccagtcct gggtatagaa     180
gtgtgaggga gagaaccagc acttctggga cgcacagaga ccgtgaagat tccaagttca    240
ggagaactcg accgttggaa tgccaagatg ccttggaaac agcagcccga gccgagggcc    300
tctctcttga tgcctccatg cattctcagc tcagaatcct ggatgaggag catcccaagg    360
gaaagtacca tcatggcttg agtgctctga gcccatccg gactacttcc aaacaccagc     420
acccagtgga caatgctggg ctttttttcct gtatgacttt ttcgtggctt tcttctctgg   480
cccgtgtggc ccacaagaag ggggagctct caatggaaga cgtgtggtct ctgtccaagc    540
acgagtcttc tgacgtgaac tgcagaagac tagagagact gtggcaagaa gagctgaatg    600
aagttgggcc agacgctgct tccctgcgaa gggttgtgtg atcttctgc cgcaccaggc     660 tcatcctgtc catcgtgtgc ctgatgatca cgcagctggc tggcttcagt ggaccagcct    720
tcatggtgaa acacctcttg gagtatacc aggcaacaga gtctaacctg cagtacagct     780
tgttgttagt gctgggcctc ctcctgacgg aaatcgtgcg gtcttggtcg cttgcactga    840
cttgggcatt gaattaccga accggtgtcc gcttgcgggg ggccatccta accatggcat    900
ttaagaagat ccttaagtta aagaacatta aagagaaatc cctgggtgag ctcatcaaca    960
tttgctccaa cgatgggcag agaatgtttg aggcagcagc cgttggcagc ctgctggctg   1020 gaggaccccgt tgttgccatc ttaggcatga tttataatgt aattattctg ggaccaacag   1080
gcttcctggg atcagctgtt tttatcctct ttacccagc aatgatgttt gcatcacggc    1140
tcacagcata tttcaggaga aaatgcgtgg ccgccacgga tgaacgtgtc cagaagatga    1200
atgaagttct tacttacatt aaatttatca aaatgtatgc ctgggtcaaa gcattttctc    1260
agagtgttca aaaaatccgc gaggaggagc gtcggatatt ggaaaaagcc gggtacttcc    1320
agggtatcac tgtgggtgtg ctcccattg tggtggtgat tgccagcgtg gtgaccttct    1380
ctgttcatat gacccctggc ttcgatctga cagcagcaca ggctttcaca gtggtgacag   1440
tcttcaattc catgacttt gctttgaaag taacaccgtt ttcagtaaag tccctctcag    1500
```

-continued

```
aagcctcagt ggctgttgac agatttaaga gtttgtttct aatggaagag gttcacatga    1560
taaagaacaa accagccagt cctcacatca agatagagat gaaaaatgcc accttggcat    1620
gggactcctc ccactccagt atccagaact cgcccaagct gacccccaaa atgaaaaaag    1680
acaagagggc ttccaggggc aagaaagaga aggtgaggca gctgcagcgc actgagcatc    1740
aggcggtgct ggcagagcag aaaggccacc tcctcctgga cagtgacgag cggcccagtc    1800
ccgaagagga agaaggcaag cacatccacc tgggccacct gcgcttacag aggacactgc    1860
acagcatcga tctggagatc caagagggta aactggttgg aatctgcggc agtgtgggaa    1920
gtggaaaaac ctctctcatt tcagccattt taggccagat gacgcttcta gagggcagca    1980
ttgcaatcag tggaaccttc gcttatgtgg cccagcaggc ctggatcctc aatgctactc    2040
tgagagacaa catcctgttt gggaaggaat atgatgaaga agatacaac tctgtgctga    2100 acagctgctg cctgaggcct gacctggcca ttcttcccag cagcgacctg acggagattg    2160
gagagcgagg agccaacctg agcggtgggc agcgccagat gatcagcctt gcccgggcct    2220
tgtatagtga caggagcatc tacatcctgg acgacccct cagtgcctta gatgcccatg    2280
tgggcaacca catcttcaat agtgctatcc ggaaacatct caagtccaag acagttctgt    2340
ttgttaccca ccagttacag tacctggttg actgtgatga agtgatcttc atgaaagagg    2400
gctgtattac ggaaagaggc acccatgagg aactgatgaa tttaaatggt gactatgcta    2460 ccattttaa taacctgttg ctgggagaga caccgccagt tgagatcaat tcaaaaaagg    2520
aaaccagtgg ttcacagaag aagtcacaag acaagggtcc taaaacagga tcagtaaaga    2580
aggaaaaagc agtaaagcca gaggaagggc agcttgtgca gctggaagag aaagggcagg    2640
gttcagtgcc ctggtcagta tatggtgtct catccaggc tgctgggggc cccttggcat    2700
tcctggttat tatggcccctt tcatgctga atgtaggcag caccgccttc agcacctggt    2760
ggttgagtta ctggatcaag caaggaagcg ggaacaccac tgtgactcga gggaacgaga    2820
cctcggtgag tgacagcatg aaggacaatc ctcatatgca gtactatgcc agcatctacg    2880
ccctctccat ggcagtcatg ctgatcctga aagccattcg aggagttgtc tttgtcaagg    2940
gcacgctgcg agcttcctcc cggctgcatg acgagctttt ccgaaggatc cttcgaagcc    3000
ctatgaagtt ttttgacacg acccccacag gaggattct caacaggttt tccaaagaca    3060
tggatgaagt tgacgtgcgg ctgccgttcc aggccgagat gttcatccag aacgttatcc    3120
tggtgttctt ctgtgtggga atgatcgcag gagtcttccc gtggttcctt gtggcagtgg    3180
ggccccttgt catcctcttt tcagtcctgc acattgtctc cagggtcctg attcgggagc    3240
tgaagcgtct ggacaatatc acgcagtcac ctttcctctc ccacatcacg tccagcatac    3300
agggccttgc caccatccac gcctacaata aagggcagga gttctgcac agataccagg    3360 agctgctgga tgacaaccaa gctccttttt ttttgtttac gtgtgcgatg cggtggctgg    3420
ctgtgcggct ggacctcatc agcatcgccc tcatcaccac cacggggctg atgatcgttc    3480
ttatgcacgg gcagattccc ccagcctatg cgggtctcgc catctcttat gctgtccagt    3540
taacggggct gttccagttt acggtcagac tggcatctga cagaagct cgattccacct    3600 cggtggagag gatcaatcac tacattaaga ctctgtcctt ggaagcacct gccagaatta    3660
agaacaaggc tccctcccct gactggcccc aggaggaga ggtgaccttt gagaacgcag    3720
agatgaggta ccgagaaaac ctccctcttg tcctaaagaa agtatccttc acgatcaaac    3780
ctaaagagaa gattggcatt gtgggggcgga caggatcagg gaagtcctcg ctggggatgg    3840
ccctcttccg tctggtggag ttatctggag gctgcatcaa gattgatgga gtgagaatca    3900
```

-continued

| | |
|---|---|
| gtgatattgg ccttgccgac ctccgaagca aactctctat cattcctcaa gagccggtgc | 3960 |
| tgttcagtgg cactgtcaga tcaaatttgg accccttcaa ccagtacact gaagaccaga | 4020 |
| tttgggatgc cctggagagg acacacatga aagaatgtat tgctcagcta cctctgaaac | 4080 |
| ttgaatctga agtgatggag aatggggata acttctcagt gggggaacgg cagctcttgt | 4140 |
| gcatagctag agccctgctc cgccactgta agattctgat tttagatgaa gccacagctg | 4200 |
| ccatggacac agagacagac ttattgattc aagagaccat ccgagaagca tttgcagact | 4260 |
| gtaccatgct gaccattgcc catcgcctgc acacggttct aggctccgat aggattatgg | 4320 |
| tgctggccca gggacaggtg gtggagtttg acccccatc ggtccttctg tccaacgaca | 4380 |
| gttcccgatt ctatgccatg tttgctgctg cagagaacaa ggtcgctgtc aagggctgac | 4440 |
| tcctccctgt tgacgaagtc tcttttcttt agagcattgc cattccctgc ctggggcggg | 4500 |
| cccctcatcg cgtcctccta ccgaaaacctt gcctttctcg attttatctt tcgcacagca | 4560 |
| gttccggatt ggcttgtgtg tttcactttt agggagagtc atattttgat tattgtattt | 4620 |
| attccatatt catgtaaaca aaatttagtt tttgttctta attgcactct aaaaggttca | 4680 |
| gggaaccgtt attataattg tatcagaggc ctataatgaa gctttatacg tgtagctata | 4740 |
| tctatatata attctgtaca tagcctatat ttacagtgaa aatgtaagct gtttatttta | 4800 |
| tattaaaata agcactgtgc taataacagt gcatattcct ttctatcatt tttgtacagt | 4860 |
| ttgctgtact agagatctgg ttttgctatt agactgtagg aagagtagca tttcattctt | 4920 |
| ctctagctgg tggtttcacg gtgccaggtt ttctgggtgt ccaaaggaag acgtgtggca | 4980 |
| atagtgggcc ctccgacagc cccctctgcc gcctccccac agccgctcca ggggtggctg | 5040 |
| gagacgggtg ggcggctgga gaccatgcag agcgccgtga ttctcaggg ctcctgcctt | 5100 |
| ctgtcctggt gtcacttact gtttctgtca ggagagcagc ggggcgaagc ccaggcccct | 5160 |
| tttcactccc tccatcaaga atggggatca cagagacatt cctccgagcc ggggagtttc | 5220 |
| tttcctgcct tcttcttttt gctgttgttt ctaaacaaga atcagtctat ccacagagag | 5280 |
| tcccactgcc tcaggttcct atggctggcc actgcacaga gctctccagc tccaagacct | 5340 |
| gttggttcca agccctggag ccaactgctg cttttgagg tggcacttt tcatttgcct | 5400 |
| attcccacac ctccacagtt cagtggcagg gctcaggatt tcgtgggtct gtttccttt | 5460 |
| ctcaccgcag tcgtcgcaca gtctctctct ctctctcccc tcaaagtctg caactttaag | 5520 |
| cagctcttgc taatcagtgt ctcacactgg cgtagaagtt tttgtactgt aaagagacct | 5580 |
| acctcaggtt gctggttgct gtgtggtttg gtgtgttccc gcaaaccccc tttgtgctgt | 5640 |
| ggggctggta gctcaggtgg gcgtggtcac tgctgtcatc agttgaatgg tcagcgttgc | 5700 |
| atgtcgtgac caactagaca ttctgtcgcc ttagcatgtt tgctgaacac cttgtggaag | 5760 |
| caaaaatctg aaaatgtgaa taaaattatt ttggattttg taaaaaaaaa aaaaaaaaa | 5820 |
| aaaaaaaaaa aaaaaaaa | 5838 |

<210> SEQ ID NO 5
<211> LENGTH: 20
<212> TYPE: DNA
<213> ORGANISM: Artificial
<220> FEATURE:
<223> OTHER INFORMATION: primer for amplification of ABCC5

<400> SEQUENCE: 5
ctagctggtg gtttcacggt                                           20

<210> SEQ ID NO 6
<211> LENGTH: 17
<212> TYPE: DNA
<213> ORGANISM: Artificial
<220> FEATURE:
<223> OTHER INFORMATION: primer for amplification of ABCC5

<400> SEQUENCE: 6
ctctgcatgg tctccag                                                   17

<210> SEQ ID NO 7
<211> LENGTH: 1709
<212> TYPE: DNA
<213> ORGANISM: Homo sapiens

<400> SEQUENCE: 7

```
ggtacctcct gccagcatct cttgggtttg ctgagaactc acgggctcca gctacctggc     60
catgaccacc acatttctgc aaacttcttc ctccaccttt ggggtggct caacccgagg    120
gggttccctc ctggctgggg gaggtggctt tggtgggggg agtctctctg ggggaggtgg    180
aagccgaagt atctcagctt cttctgctag gtttgtctct tcagggtcag gaggaggata    240
tgggggtggc atgagggtct gtggctttgg tgagggggct ggtagtgttt tcggtggagg    300
ctttggaggg ggcgttggtg ggggttttgg tggtggcttt ggtggtggcg atggtggtct    360
cctctctggc aatgagaaaa ttaccatgca gaacctcaat gaccgcctgg cctcctacct    420
ggacaaggta cgtgccctgg aggaggccaa tgctgacctg gaggtgaaga tccatgactg    480
gtaccagaag cagacccccaa ccagcccaga atgcgactac agccaatact tcaagaccat    540
tgaagagctc cgggacaaga tcatggccac caccatcgac aactcccggg tcatcctgga    600
gatcgacaat gccaggctgg ctgcggacga cttcaggctc aagtatgaga atgagctggc    660
cctgcgccag ggcgttgagg ctgacatcaa cggcttgcgc cgagtcctgg atgagctgac    720
cctggccagg actgacctgg agatgcagat cgagggcctg aatgaggagc tagcctacct    780
gaagaagaac cacgaagagg agatgaagga gttcagcagc cagctggccg gccaggtcaa    840
tgtggagatg gacgcagcac cgggtgtgga cctgacccgt gtgctggcag agatgaggga    900
gcagtacgag gccatggcgg agaagaaccg ccgggatgtc gaggcctggt tcttcagcaa    960
gactgaggag ctgaacaaag aggtggcctc caacacagaa atgatccaga ccagcaagac   1020
ggagatcaca gacctgagac gcacgatgca ggagctggag atcgagctgc agtcccagct   1080
cagcatgaaa gctgggctgg agaactcact ggccgagaca gagtgccgct atgccacgca   1140
gctgcagcag atccagggc tcattggtgg cctggaggcc cagctgagtg agctccgatg   1200
cgagatggag gctcagaacc aggagtacaa gatgctgctt gacataaaga cacggctgga   1260
gcaggagatc gctacttacc gcagcctgct cgagggccag gatgccaaga tggctggcat   1320
tggcatcagg gaagcctctt caggaggtgg tggtagcagc agcaatttcc acatcaatgt   1380
agaagagtca gtggatggac aggtggtttc ttcccacaag agagaaatct aagtgtctat   1440
tgcaggagaa acgtcccttg ccactcccca ctctcatcag gccaagtgga ggactggcca   1500
gagggcctgc acatgcaaac tccagtccct gccttcagag agctgaaaag ggtccctcgg   1560
tcttttattt cagggctttg catgcgctct attccccctc tgcctctccc cacccttctt   1620
ggagcaagga gatgcagctg tattgtgtaa caagctcatt tgtacagtgt ctgttcatgt   1680
aataaagaat tacttttcct tttgcaaat                                     1709
```

<210> SEQ ID NO 8
<211> LENGTH: 18
<212> TYPE: DNA
<213> ORGANISM: Artificial
<220> FEATURE:
<223> OTHER INFORMATION: primer for amplification of KRT15

<400> SEQUENCE: 8
ggaggggctg gtagtgtt                                                18

<210> SEQ ID NO 9
<211> LENGTH: 18
<212> TYPE: DNA
<213> ORGANISM: Artificial
<220> FEATURE:
<223> OTHER INFORMATION: primer for amplification of KRT15

<400> SEQUENCE: 9
accttgtcca ggtaggag                                                18

<210> SEQ ID NO 10
<211> LENGTH: 1634
<212> TYPE: DNA
<213> ORGANISM: Homo sapiens

<400> SEQUENCE: 10

| | | |
|---|---|---|
| acccgagcac cttctcttca ctcagccaac tgctcgctcg ctcacctccc tcctctgcac | 60 |
| catgactacc tgcagccgcc agttcacctc ctccagctcc atgaagggct cctgcggcat | 120 |
| cgggggcggc atcggggggcg gctccagccg catctcctcc gtcctggccg agggtcctg | 180 |
| ccgcgcccc agcacctacg ggggcggcct gtctgtctca tcctcccgct tctcctctgg | 240 |
| gggagcctac gggctggggg gcggctatgg cggtggcttc agcagcagca gcagcagctt | 300 |
| tggtagtggc tttggggggag atatggtgg tggccttggt gctggcttgg gtggtggctt | 360 |
| tggtggtggc tttgctggtg gtgatgggct tctggtgggc agtgagaagg tgaccatgca | 420 |
| gaacctcaat gaccgcctgg cctcctacct ggacaaggtg cgtgctctgg aggaggccaa | 480 |
| cgccgacctg gaagtgaaga tccgtgactg gtaccagagg cagcggcctg ctgagatcaa | 540 |
| agactacagt ccctacttca gaccattga ggacctgagg aacaagattc tcacagccac | 600 |
| agtggacaat gccaatgtcc ttctgcagat tgacaatgcc cgtctggccg cggatgactt | 660 |
| ccgcaccaag tatgagacag agttgaacct gcgcatgagt gtggaagccg acatcaatgg | 720 |
| cctgcgcagg gtgctggacg aactgaccct ggccagagct gacctggaga tgcagattga | 780 |
| gagcctgaag gaggagctgg cctacctgaa gaagaaccac gaggaggaga tgaatgccct | 840 |
| gagaggccag gtgggtggag atgtcaatgt ggagatggac gctgcacctg cgtggaccct | 900 |
| gagccgcatt ctgaacgaga tgcgtgacca gtatgagaag atggcagaga gaaccgcaa | 960 |
| ggatgccgag gaatggttct tcaccaagac agaggagctg aaccgcgagg tggccaccaa | 1020 |
| cagcgagctg gtgcagagcg gcaagagcga gatctcggag ctccggcgca ccatgcagaa | 1080 |
| cctggagatt gagctgcagt cccagctcag catgaaagca tccctggaga cagcctgga | 1140 |
| ggagaccaaa ggtcgctact gcatgcagct ggcccagatc caggagatga ttggcagcgt | 1200 |
| ggaggagcag ctggcccagc tccgctgcga tgatggcag cagaaccagg agtacaagat | 1260 |
| cctgctggac gtgaagacgc ggctggagca ggagatcgcc acctaccgcc gcctgctgga | 1320 |
| gggcgaggac gcccacctct cctcctccca gttctcctct ggatcgcagt catccagaga | 1380 |
| tgtgacctcc tccagccgcc aaatccgcac caaggtcatg gatgtgcacg atggcaaggt | 1440 |

-continued

| | |
|---|---|
| ggtgtccacc cacgagcagg tccttcgcac caagaactga ggctgcccag ccccgctcag | 1500 |
| gcctaggagg ccccccgtgt ggacacagat cccactggaa gatcccctct cctgcccaag | 1560 |
| cacttcacag ctggaccctg cttcaccctc accccctcct ggcaatcaat acagcttcat | 1620 |
| tatctgagtt gcat | 1634 |

<210> SEQ ID NO 11
<211> LENGTH: 20
<212> TYPE: DNA
<213> ORGANISM: Artificial
<220> FEATURE:
<223> OTHER INFORMATION: primer for amplification of KRT14

<400> SEQUENCE: 11

| | |
|---|---|
| agatggagca gcagaaccag | 20 |

<210> SEQ ID NO 12
<211> LENGTH: 19
<212> TYPE: DNA
<213> ORGANISM: Artificial
<220> FEATURE:
<223> OTHER INFORMATION: primer for amplification of KRT14

<400> SEQUENCE: 12

| | |
|---|---|
| tggaggaggg tcvacatct | 19 |

<210> SEQ ID NO 13
<211> LENGTH: 3018
<212> TYPE: DNA
<213> ORGANISM: Homo sapiens

<400> SEQUENCE: 13

| | |
|---|---|
| ctcctcacag gtgtgtctct agtcctcgtg gttgcctgcc ccactccctg ccgagacgcc | 60 |
| tgccagaaag gtcacctatc ctgaacccca gcaagcctga acagctcag ccaagcaccc | 120 |
| tgcgatggaa gctgcagatg cctccaggag caacgggtcg agcccagaag ccagggatgc | 180 |
| ccggagcccg tcgggcccca gtggcagcct ggagaatggc accaaggctg acggcaagga | 240 |
| tgccaagacc accaacgggc acggcgggga ggcagctgag ggcaagagcc tgggcagcgc | 300 |
| cctgaagcca ggggaaggta ggagcgcct gttcgcgggc aatgagtggc ggcgacccat | 360 |
| catccagttt gtcgagtccg gggacgacaa gaactccaac tacttcagca tggactctat | 420 |
| ggaaggcaag aggtcgccgt acgcagggct ccagctgggg gctgccaaga agccacccgt | 480 |
| tacctttgcc gaaaagggcg agctgcgcaa gtccattttc tcggagtccc ggaagcccac | 540 |
| ggtgtccatc atggagcccg gggagacccg gcggaacagc taccccgggg ccgacacggg | 600 |
| cctttttttca cggtccaagt ccggctccga ggaggtgctg tgcgactcct gcatcggcaa | 660 |
| caagcagaag gcggtcaagt cctgcctggt gtgccaggcc tccttctgcg agctgcatct | 720 |
| caagccccac ctgagggggcg ccgccttccg agaccaccag ctgctcgagc catccgggga | 780 |
| ctttgaggcc cgcaagtgtc ccgtgcatgg caagacgatg gagctcttct gccagaccga | 840 |
| ccagacctgc atctgctacc tttgcatgtt ccaggagcac aagaatcata gcaccgtgac | 900 |
| agtggaggag gccaaggccg agaaggagac ggagctgtca ctgcaaaagg agcagctgca | 960 |
| gctcaagatc attgagattg aggatgaagc tgagaagtgg cagaaggaga aggaccgcat | 1020 |
| caagagcttc accaccaatg agaaggccat cctggagcag aacttccggg acctggtgcg | 1080 |
| ggacctggag aagcaaaagg aggaagtgag ggctgcgctg gagcagcggg agcaggatgc | 1140 |
| tgtggaccaa gtgaaggtga tcatggatgc tctggatgag agagccaagg tgctgcatga | 1200 |

-continued

```
ggacaagcag acccgggagc agctgcatag catcagcgac tctgtgttgt ttctgcagga    1260
atttggtgca ttgatgagca attactctct cccccacccc ctgcccacct atcatgtcct    1320
gctggagggg gagggcctgg gacagtcact aggcaacttc aaggacgacc tgctcaatgt    1380
atgcatgcgc cacgttgaga gatgtgcaa ggcggacctg agccgtaact tcattgagag    1440
gaaccacatg gagaacggtg gtgaccatcg ctatgtgaac aactacacga acagcttcgg    1500
gggtgagtgg agtgcaccgg acaccatgaa gagatactcc atgtacctga cacccaaagg    1560
tggggtccgg acatcatacc agccctcgtc tcctggccgc ttcaccaagg agaccaccca    1620
gaagaatttc aacaatctct atggcaccaa aggtaactac acctcccggg tctgggagta    1680
ctcctccagc attcagaact ctgacaatga cctgcccgtc gtccaaggca gctcctcctt    1740
ctccctgaaa ggctatccct ccctcatgcg gagccaaagc cccaaggccc agccccagac    1800
ttggaaatct ggcaagcaga ctatgctgtc tcactaccgg ccattctacg tcaacaaagg    1860
caacgggatt gggtccaacg aagcccccatg agctcctggc ggaaggaacg aggcgccaca    1920
cccctgctct tcctcctgac cctgctgctc ttgccttcta agctactgtg cttgtctggg    1980
tgggagggag cctggtcctg cacctgccct ctgcagccct ctgccagcct cttggggca    2040 gttccggcct ctccgacttc cccactggcc acactccatt cagactcctt tcctgccttg    2100
tgacctcaga tggtcaccat cattcctgtg ctcagaggcc aacccatcac aggggtgaga    2160
taggttgggg cctgccctaa cccgccagcc tcctcctctc gggctggatc tgggggctag    2220
cagtgagtac ccgcatggta tcagcctgcc tctcccgccc acgccctgct gtctccaggc    2280
ctatagacgt ttctctccaa ggccctatcc cccaatgttg tcagcagatg cctggacagc    2340
acagccaccc atctcccatt cacatggccc acctcctgct tcccagagga ctggccctac    2400
gtgctctctc tcgtcctacc tatcaatgcc cagcatggca gaacctgcag cccttggcca    2460
ctgcagatgg aaacctctca gtgtcttgac atcaccctac ccaggcggtg ggtctccacc    2520
acagccactt tgagtctgtg gtccctggag ggtggcttct cctgactggc aggatgacct    2580
tagccaagat attcctctgt tccctctgct gagataaaga attcccttaa catgatataa    2640
tccacccatg caaatagcta ctggcccagc taccatttac catttgccta cagaatttca    2700
ttcagtctac actttggcat tctctctggc gatggagtgt ggctgggctg accgcaaaag    2760
gtgccttaca cactgccccc accctcagcc gttgccccat cagaggctgc ctcctccttc    2820
tgattacccc ccatgttgca tatcagggtg ctcaaggatt ggagaggaga caaaaccagg    2880
agcagcacag tggggacatc tcccgtctca acagcccag gcctatgggg gctctggaag    2940
gatgggccag cttgcagggg ttggggaggg agacatccag cttgggcttt ccccttttgga   3000 ataaaccatt ggtctgtc                                                  3018
```

<210> SEQ ID NO 14
<211> LENGTH: 18
<212> TYPE: DNA
<213> ORGANISM: Artificial
<220> FEATURE:
<223> OTHER INFORMATION: primer for amplification of TRIM29

<400> SEQUENCE: 14

```
aaggtgcctt acacactg                                                    18
```

<210> SEQ ID NO 15
<211> LENGTH: 17
<212> TYPE: DNA

```
<213> ORGANISM: Artificial
<220> FEATURE:
<223> OTHER INFORMATION: primer for amplification of TRIM29

<400> SEQUENCE: 15
ggctgttgag acgggag                                                    17

<210> SEQ ID NO 16
<211> LENGTH: 2558
<212> TYPE: DNA
<213> ORGANISM: Homo sapiens

<400> SEQUENCE: 16
ttgtgctcct cgcttgcctg ttccttttcc acgcattttc caggataact gtgactccag       60
gcccgcaatg gatgccctgc aactagcaaa ttcggctttt gccgttgatc tgttcaaaca      120
actatgtgaa aaggagccac tgggcaatgt cctcttctct ccaatctgtc tctccacctc      180
tctgtcactt gctcaagtgg gtgctaaagg tgacactgca aatgaaattg gacaggttct      240
tcattttgaa aatgtcaaag atataccctt tggatttcaa acagtaacat cggatgtaaa      300
caaacttagt tccttttact cactgaaact aatcaagcgg ctctacgtag acaaatctct      360
gaatctttct acagagttca tcagctctac gaagagaccc tatgcaaagg aattggaaac      420
tgttgacttc aaagataaat tggaagaaac gaaaggtcag atcaacaact caattaagga      480
tctcacagat ggccactttg agaacatttt agctgacaac agtgtgaacg accagaccaa      540
aatccttgtg ttaatgctgc ctactttgt tggcaagtgg atgaagaaat ttcctgaatc      600
agaaacaaaa gaatgtcctt tcagactcaa caagacagac accaaaccag tgcagatgat      660
gaacatggag gccacgttct gtatgggaaa cattgacagt atcaattgta agatcataga      720
gcttcctttt caaaataagc atctcagcat gttcatccta ctacccaagg atgtggagga      780
tgagtccaca ggcttggaga agattgaaaa acaactcaac tcagagtcac tgtcacagtg      840
gactaatccc agcaccatgg ccaatgccaa ggtcaaactc tccattccaa aatttaaggt      900
ggaaaagatg attgatccca aggcttgtct ggaaaatcta gggctgaaac atatcttcag      960
tgaagacaca tctgatttct ctggaatgtc agagaccaag ggagtggccc tatcaaatgt     1020
tatccacaaa gtgtgcttag aaataactga agatggtggg gattccatag aggtgccagg     1080
agcacggatc ctgcagcaca aggatgaatt gaatgctgac catcccttta tttacatcat     1140
caggcacaac aaaactcgaa acatcatttt ctttggcaaa ttctgttctc cttaagtggc     1200
atagcccatg ttaagtcctc cctgactttt ctgtggatgc cgatttctgt aaactctgca     1260
tccagagatt cattttctag atacaataaa ttgctaatgt tgctggatca ggaagccgcc     1320
agtacttgtc atatgtagcc ttcacacaga tagacctttt tttttttcca attctatctt     1380
ttgtttcctt ttttcccata agacaatgac atacgctttt aatgaaaagg aatcacgtta     1440
gaggaaaaat atttattcat tatttgtcaa attgtccggg gtagtggca gaaatacagt     1500 cttccacaaa gaaaattcct ataaggaaga tttggaagct cttcttccca gcactatgct     1560
ttccttcttt gggatagaga atgttccaga cattctcgct tccctgaaag actgaagaaa     1620
gtgtagtgca tgggacccac gaaactgccc tggctccagt gaaacttggg cacatgctca     1680
ggctactata ggtccagaag tcctatgtt aagcccctggc aggcaggtgt ttattaaaat     1740
tctgaatttt ggggattttc aaaagataat attttacata cactgtatgt tatagaactt     1800
catggatcag atctggggca gcaacctata aatcaacacc ttaatatgct gcaacaaaat     1860
gtagaatatt cagacaaaat ggatacataa agactaagta gcccataagg ggtcaaaatt     1920
```

-continued

| | |
|---|---|
| tgctgccaaa tgcgtatgcc accaacttac aaaaacactt cgttcgcaga gcttttcaga | 1980 |
| ttgtggaatg ttggataagg aattatagac ctctagtagc tgaaatgcaa gaccccaaga | 2040 |
| ggaagttcag atcttaatat aaattcactt tcatttttga tagctgtccc atctggtcat | 2100 |
| gtggttggca ctagactggt ggcaggggct tctagctgac tcgcacaggg attctcacaa | 2160 |
| tagccgatat cagaatttgt gttgaaggaa cttgtctctt catctaatat gatagcggga | 2220 |
| aaaggagagg aaactactgc ctttagaaaa tataagtaaa gtgattaaag tgctcacgtt | 2280 |
| accttgacac atagtttttc agtctatggg tttagttact ttagatggca agcatgtaac | 2340 |
| ttatattaat agtaatttgt aaagttgggt ggataagcta tccctgttgc cggttcatgg | 2400 |
| attacttctc tataaaaaat atatatttac caaaaatttt tgtgacattc cttctcccat | 2460 |
| ctcttccttg acatgcattg taaataggtt cttcttgttc tgagattcaa tattgaattt | 2520 |
| ctcctatgct attgacaata aaatattatt gaactacc | 2558 |

<210> SEQ ID NO 17
<211> LENGTH: 20
<212> TYPE: DNA
<213> ORGANISM: Artificial
<220> FEATURE:
<223> OTHER INFORMATION: primer for amplification of SERPINB5

<400> SEQUENCE: 17
gccgatatca gaatttgtgt          20

<210> SEQ ID NO 18
<211> LENGTH: 25
<212> TYPE: DNA
<213> ORGANISM: Artificial
<220> FEATURE:
<223> OTHER INFORMATION: primer for amplification of SERPINB5

<400> SEQUENCE: 18
gccatctaaa gtaactaaac ccata          25

<210> SEQ ID NO 19
<211> LENGTH: 1421
<212> TYPE: DNA
<213> ORGANISM: Homo sapiens

<400> SEQUENCE: 19

| | |
|---|---|
| acttactgcg ggacggcctt ggagagtact cgggttcgtg aacttcccgg aggcgcaatg | 60 |
| agctgcatta acctgcccac tgtgctgccc ggctccccca gcaagacccg ggggcagatc | 120 |
| caggtgattc tcgggccgat gttctcagga aaaagcacag agttgatgag acgcgtccgt | 180 |
| cgcttccaga ttgctcagta caagtgcctg gtgatcaagt atgccaaaga cactcgctac | 240 |
| agcagcagct tctgcacaca tgaccggaac accatggagg cgctgcccgc ctgcctgctc | 300 |
| cgagacgtgg cccaggaggc cctgggcgtg gctgtcatag catcgacga ggggcagttt | 360 |
| ttccctgaca tcatggagtt ctgcgaggcc atggccaacg ccgggaagac cgtaattgtg | 420 |
| gctgcactgg atgggacctt ccagaggaag ccatttgggg ccatcctgaa cctggtgccg | 480 |
| ctggccgaga gcgtggtgaa gctgacggcg gtgtgcatgg agtgcttccg ggaagccgcc | 540 |
| tataccaaga ggctcggcac agagaaggag gtcgaggtga ttgggggagc agacaagtac | 600 |
| cactccgtgt gtcggctctg ctacttcaag aaggcctcag gccagcctgc cgggccggac | 660 |
| aacaaagaga actgcccagt gccaggaaag ccaggggaag ccgtggctgc caggaagctc | 720 |

-continued

| | |
|---|---|
| tttgccccac agcagattct gcaatgcagc cctgccaact gagggacctg caagggccgc | 780 |
| ccgctccctt cctgccactg ccgcctactg gacgctgccc tgcatgctgc ccagccactc | 840 |
| caggaggaag tcgggaggcg tggagggtga ccacaccttg gccttctggg aactctcctt | 900 |
| tgtgtggctg ccccacctgc cgcatgctcc ctcctctcct acccactggt ctgcttaaag | 960 |
| cttccctctc agctgctggg acgatcgccc aggctggagc tggccccgct tggtggcctg | 1020 |
| ggatctggca cactccctct ccttggggtg agggacagag cccacgctg ttgacatcag | 1080 |
| cctgcttctt cccctctgcg gctttcactg ctgagtttct gttctccctg ggaagcctgt | 1140 |
| gccagcacct ttgagccttg gcccacactg aggcttaggc ctctctgcct gggatgggct | 1200 |
| cccacccctcc cctgaggatg gcctggattc acgccctctt gtttccttt gggctcaaag | 1260 |
| cccttcctac ctctggtgat ggtttccaca ggaacaacag catctttcac caagatgggt | 1320 |
| ggcaccaacc ttgctgggac ttggatccca ggggcttatc tcttcaagtg tggagagggc | 1380 |
| agggtccacg cctctgctgt agcttatgaa attaactaat t | 1421 |

<210> SEQ ID NO 20
<211> LENGTH: 18
<212> TYPE: DNA
<213> ORGANISM: Artificial
<220> FEATURE:
<223> OTHER INFORMATION: primer for amplification of TK1

<400> SEQUENCE: 20

| | |
|---|---|
| cagagaagga ggtcgagg | 18 |

<210> SEQ ID NO 21
<211> LENGTH: 16
<212> TYPE: DNA
<213> ORGANISM: Artificial
<220> FEATURE:
<223> OTHER INFORMATION: primer for amplification of TK1

<400> SEQUENCE: 21

| | |
|---|---|
| gcaaagagct tcctgg | 16 |

<210> SEQ ID NO 22
<211> LENGTH: 1024
<212> TYPE: DNA
<213> ORGANISM: Homo sapiens

<400> SEQUENCE: 22

| | |
|---|---|
| cttcctggct cctccttcct ccccacccct ctaataggct cataagtggg ctcaggcctc | 60 |
| tctgcgggc tcactctgcg cttcaccatg gctttcattg ccaagtcctt ctatgacctc | 120 |
| agtgccatca gcctggatgg ggagaaggta gatttcaata cgttccgggg cagggccgtg | 180 |
| ctgattgaga atgtggcttc gctctgaggc acaaccaccc gggacttcac ccagctcaac | 240 |
| gagctgcaat gccgctttcc caggcgcctg gtggtccttg gcttcccttg caaccaattt | 300 |
| ggacatcagg agaactgtca gaatgaggag atcctgaaca gtctcaagta tgtccgtcct | 360 |
| gggggtggat accagcccac cttcacccctt gtccaaaaat gtgaggtgaa tgggcagaac | 420 |
| gagcatcctg tcttcgccta cctgaaggac aagctcccct acccttatga tgacccattt | 480 |
| tccctcatga ccgatcccaa gctcatcatt tggagccctg tgcgccgctc agatgtggcc | 540 |
| tggaactttg agaagttcct catagggccg gagggagagc cttccgacg ctacagccgc | 600 |
| accttcccaa ccatcaacat tgagcctgac atcaagcgcc tccttaaagt tgccatatag | 660 |
| atgtgaactg ctcaacacac agatctccta ctccatccag tcctgaggag ccttaggatg | 720 |

-continued

```
cagcatgcct tcaggagaca ctgctggacc tcagcattcc cttgatatca gtccccttca      780
ctgcagagcc ttgcctttcc cctctgcctg tttccttttc ctctcccaac cctctggttg      840
gtgattcaac ttgggctcca agacttgggt aagctctggg ccttcacaga atgatggcac      900
cttcctaaac cctcatgggt ggtgtctgag aggcgtgaag ggcctggagc cactctgcta      960
gaagagacca ataaagggca ggtgtggaaa cggcaaaaaa aaaaaaaaaa aaaaaaaaa      1020 aaaa                                                                   1024
```

<210> SEQ ID NO 23
<211> LENGTH: 18
<212> TYPE: DNA
<213> ORGANISM: Artificial
<220> FEATURE:
<223> OTHER INFORMATION: primer for amplification of GPX2

<400> SEQUENCE: 23

```
caagcgcctc cttaaagt                                                    18
```

<210> SEQ ID NO 24
<211> LENGTH: 18
<212> TYPE: DNA
<213> ORGANISM: Artificial
<220> FEATURE:
<223> OTHER INFORMATION: primer for amplification of GPX2

<400> SEQUENCE: 24

```
ctgcagtgaa ggggactg                                                    18
```

<210> SEQ ID NO 25
<211> LENGTH: 1973
<212> TYPE: DNA
<213> ORGANISM: Homo sapiens

<400> SEQUENCE: 25

```
gggatattgg agtagcaaga ggctgggaag ccatcactta ccttgcactg agaaagaaga       60
caaaggccag tatgcacagc tttcctccac tgctgctgct gctgttctgg ggtgtggtgt      120
ctcacagctt cccagcgact ctagaaacac aagagcaaga tgtggactta gtccagaaat      180
acctggaaaa atactacaac ctgaagaatg atgggaggca agttgaaaag cggagaaata      240
gtggcccagt ggttgaaaaa ttgaagcaaa tgcaggaatt ctttgggctg aaagtgactg      300 gaaaccaga tgctgaaacc ctgaaggtga tgaagcagcc cagatgtgga gtgcctgatg      360
tggctcagtt tgtcctcact gaggggaacc ctcgctggga gcaaacacat ctgacctaca      420
ggattgaaaa ttcacgcca gatttgccaa gagcagatgt ggaccatgcc attgagaaag      480
ccttccaact ctggagtaat gtcacacctc tgacattcac caaggtctct gagggtcaag      540
cagacatcat gatatctttt gtcagggag atcatcggga caactctcct tttgatggac      600
ctggaggaaa tcttgctcat gctttcaac caggcccagg tattggaggg gatgctcatt      660
ttgatgaaga tgaaaggtgg accaacaatt tcagagagta caacttacat cgtgttgcgg      720
ctcatgaact cggccattct cttggactct cccattctac tgatatcggg gctttgatgt      780
accctagcta caccttcagt ggtgatgttc agctagctca ggatgacatt gatggcatcc      840
aagccatata tggacgttcc caaaatcctg tccagcccat cggcccacaa accccaaaag      900
cgtgtgacag taagctaacc tttgatgcta taactacgat tcgggagaa gtgatgttct      960 ttaaagacag attctacatg cgcacaaatc ccttctaccc ggaagttgag ctcaatttca     1020
```

-continued

| | |
|---|---|
| tttctgtttt ctggccacaa ctgccaaatg ggcttgaagc tgcttacgaa tttgccgaca | 1080 |
| gagatgaagt ccggttttc aaagggaata agtactgggc tgttcaggga cagaatgtgc | 1140 |
| tacacggata ccccaaggac atctacagct cctttggctt ccctagaact gtgaagcata | 1200 |
| tcgatgctgc tctttctgag gaaaacactg gaaaaaccta cttctttgtt gctaacaaat | 1260 |
| actggaggta tgatgaatat aaacgatcta tggatccagg ttatcccaaa atgatagcac | 1320 |
| atgactttcc tggaattggc cacaaagttg atgcagtttt catgaaagat ggattttct | 1380 |
| atttctttca tggaacaaga caatacaaat ttgatcctaa aacgaagaga attttgactc | 1440 |
| tccagaaagc taatagctgg ttcaactgca ggaaaaattg aacattacta atttgaatgg | 1500 |
| aaaacacatg gtgtgagtcc aagaaggtg ttttcctgaa gaactgtcta ttttctcagt | 1560 |
| cattttaac ctctagagtc actgatacac agaatatat cttatttata cctcagtttg | 1620 |
| catatttttt tactatttag aatgtagccc ttttgtact gatataattt agttccacaa | 1680 |
| atggtgggta caaaaagtca agtttgtggc ttatggattc atataggcca gagttgcaaa | 1740 |
| gatcttttcc agagtatgca actctgacgt tgatcccaga gagcagcttc agtgacaaac | 1800 |
| atatcctttc aagacagaaa gagacaggag acatgagtct tgccggagg aaaagcagct | 1860 |
| caagaacaca tgtgcagtca ctggtgtcac cctggatagg caagggataa ctcttctaac | 1920 |
| acaaataag tgttatatgt ttggaataaa gtcaaccttg tttctactgt ttt | 1973 |

<210> SEQ ID NO 26
<211> LENGTH: 18
<212> TYPE: DNA
<213> ORGANISM: Artificial
<220> FEATURE:
<223> OTHER INFORMATION: primer for amplification of MMP1

<400> SEQUENCE: 26
cccaaaagcg tgtgacag    18

<210> SEQ ID NO 27
<211> LENGTH: 20
<212> TYPE: DNA
<213> ORGANISM: Artificial
<220> FEATURE:
<223> OTHER INFORMATION: primer for amplification of MMP1

<400> SEQUENCE: 27
cagttgtggc cagaaaacag    20

<210> SEQ ID NO 28
<211> LENGTH: 5925
<212> TYPE: DNA
<213> ORGANISM: Homo sapiens

<400> SEQUENCE: 28

| | |
|---|---|
| gcgctgcccg cctcgtcccc accccccaa ccccgcgcc cgccctcgga cagtccctgc | 60 |
| tcgcccgcgc gctgcagccc catctcctag cggcagccca ggcgcggagg gagcgagtcc | 120 |
| gccccgaggt aggtccagga cgggcgcaca gcagcagccg aggctggccg ggagagggag | 180 |
| gaagaggatg gcagggccac gccccagccc atgggccagg ctgctcctgg cagccttgat | 240 |
| cagcgtcagc ctctctggga ccttggcaaa ccgctgcaag aaggcccag tgaagagctg | 300 |
| cacggagtgt gtccgtgtgg ataaggactg cgcctactgc acagacgaga tgttcaggga | 360 |
| ccggcgctgc aacaccccag gcggagctgct ggccgcgggc tgccagcggg agagcatcgt | 420 |
| ggtcatggag agcagcttcc aaatcacaga ggagacccag attgacacca ccctgcggcg | 480 |

```
cagccagatg tcccccaag gcctgcgggt ccgtctgcgg cccggtgagg agcggcattt    540
tgagctggag gtgtttgagc cactggagag ccccgtggac ctgtacatcc tcatggactt    600
ctccaactcc atgtccgatg atctggacaa cctcaagaag atggggcaga acctggctcg    660
ggtcctgagc cagctcacca gcgactacac tattggattt ggcaagtttg tggacaaagt    720
cagcgtcccg cagacggaca tgaggcctga aagctgaag gagccctggc caacagtga    780
cccccccttc tccttcaaga acgtcatcag cctgacagaa gatgtggatg agttccggaa    840
taaactgcag ggagagcgga tctcaggcaa cctggatgct cctgagggcg gcttcgatgc    900
catcctgcag acagctgtgt gcacgaggga cattggctgg cgcccggaca gcacccacct    960
gctggtcttc tccaccgagt cagccttcca ctatgaggct gatggcgcca acgtgctggc    1020
tggcatcatg agccgcaacg atgaacggtg ccacctggac accacgggca cctacaccca    1080
gtacaggaca caggactacc cgtcggtgcc caccctggtg cgcctgctcg ccaagcacaa    1140
catcatcccc atctttgctg tcaccaacta ctcctatagc tactacgaga agcttcacac    1200
ctatttccct gtctcctcac tggggtgct gcaggaggac tcgtccaaca tcgtggagct    1260
gctggaggag gccttcaatc ggatccgctc caacctggac atccgggccc tagacagccc    1320
ccgaggcctt cggacagagg tcacctccaa gatgttccag aagacgagga ctgggtcctt    1380
tcacatccgg cgggggaag tgggtatata ccaggtgcag ctgcgggccc ttgagcacgt    1440
ggatgggacg cacgtgtgcc agctgccgga ggaccagaag ggcaacatcc atctgaaacc    1500
ttccttctcc gacggcctca agatggacgc gggcatcatc tgtgatgtgt gcacctgcga    1560
gctgcaaaaa gaggtgcggt cagctcgctg cagcttcaac ggagacttcg tgtgcggaca    1620
gtgtgtgtgc agcgagggct ggagtggcca gacctgcaac tgctccaccg gctctctgag    1680
tgacattcag ccctgcctgc gggagggcga ggacaagccg tgctccggcc gtggggagtg    1740
ccagtgcggg cactgtgtgt gctacggcga aggccgctac gagggtcagt ctgcgagta    1800
tgacaacttc cagtgtcccc gcacttccgg gttcctctgc aatgaccgag gacgctgctc    1860
catgggccag tgtgtgtgtg agcctggttg gacaggccca agctgtgact gtcccctcag    1920
caatgccacc tgcatcgaca gcaatggggg catctgtaat ggacgtggcc actgtgagtg    1980
tggccgctgc cactgccacc agcagtcgct ctacacggac accatctgcg agatcaacta    2040
ctcggcgatc caccccgggcc tctgcgagga cctacgctcc tgcgtgcagt gccaggcgtg    2100
gggcaccggc gagaagaagg ggcgcacgtg tgaggaatgc aacttcaagg tcaagatggt    2160
ggacgagctt aagagagccg aggaggtggt ggtgcgctgc tccttccggg acgaggatga    2220
cgactgcacc tacagctaca ccatggaagg tgacggcgcc cctgggccca acagcactgt    2280
cctggtgcac aagaagaagg actgccctcc gggctccttc tggtggctca tcccctgct    2340
cctcctcctc ctgccgctcc tggccctgct actgctgcta tgctgaagt actgtgcctg    2400
ctgcaaggcc tgcctggcac ttctcccgtg ctgcaaccga ggtcacatgg tgggctttaa    2460
ggaagaccac tacatgctgc gggagaacct gatggcctct gaccacttgg acacgcccat    2520
gctgcgcagc gggaacctca agggccgtga cgtggtccgc tggaaggtca ccaacaacat    2580
gcagcggcct ggctttgcca ctcatgccgc cagcatcaac cccacagagc tggtgcccta    2640
cgggctgtcc ttgcgcctgg cccgcctttg caccgagaac ctgctgaagc ctgacactcg    2700
ggagtgcgcc cagctgcgcc aggaggtgga ggagaacctg aacgaggtct acaggcagat    2760
ctccggtgta cacaagctcc agcagaccaa gttccggcag cagcccaatg ccgggaaaaa    2820
```

```
gcaagaccac accattgtgg acacagtgct gatggcgccc cgctcggcca agccggccct    2880
gctgaagctt acagagaagc aggtggaaca gagggccttc cacgacctca aggtggcccc    2940
cggctactac accctcactg cagaccagga cgcccgggcc atggtggagt tccaggaggg    3000
cgtggagctg gtggacgtac gggtgcccct ctttatccgg cctgaggatg acgacgagaa    3060
gcagctgctg gtggaggcca tcgacgtgcc cgcaggcact gccaccctcg gccgccgcct    3120
ggtaaacatc accatcatca aggagcaagc cagagacgtg gtgtcctttg agcagcctga    3180
gttctcggtc agccgcgggg accaggtggc ccgcatccct gtcatccggc gtgtcctgga    3240
cggcgggaag tcccaggtct cctaccgcac acaggatggc accgcgcagg caaccggga    3300
ctacatcccc gtggagggtg agctgctgtt ccagcctggg gaggcctgga aagagctgca    3360
ggtgaagctc ctggagctgc aagaagttga ctccctcctg cggggccgcc aggtccgccg    3420
tttccacgtc cagctcagca accctaagtt tggggcccac ctgggccagc ccactccac    3480
caccatcatc atcagggacc cagatgaact ggaccggagc ttcacgagtc agatgttgtc    3540
atcacagcca ccccctcacg gcgacctggg cgccccgcag aaccccaatg ctaaggccgc    3600
tgggtccagg aagatccatt tcaactggct gccccttct ggcaagccaa tggggtacag    3660
ggtaaagtac tggattcagg gtgactccga atccgaagcc cacctgctcg acagcaaggt    3720
gccctcagtg gagctcacca acctgtaccc gtattgcgac tatgagatga aggtgtgcgc    3780
ctacgggct cagggcgagg gaccctacag ctccctggtg tcctgccgca cccaccagga    3840
agtgcccagc gagccagggc gtctggcctt caatgtcgtc cctccacgg tgacccagct    3900
gagctgggct gagccggctg agaccaacgg tgagatcaca gcctacgagg tctgctatgg    3960
cctggtcaac gatgacaacc gacctattgg gcccatgaag aaagtgctgg ttgacaaccc    4020
taagaaccgg atgctgctta ttgagaacct tcgggagtcc cagccctacc gctacacggt    4080
gaaggcgcgc aacggggccg gctgggggcc tgagcgggag gccatcatca acctggccac    4140
ccagcccaag aggcccatgt ccatccccat catccctgac atccctatcg tggacgccca    4200
gagcggggag gactacgaca gcttccttat gtacagcgat gacgttctac gctctccatc    4260
gggcagccag aggcccagcg tctccgatga cactggctgc ggctggaagt cgagcccct    4320
gctgggggag gagctggacc tgcggcgcgt cacgtggcgg ctgccccgg agctcatccc    4380
gcgcctgtcg gccagcagcg ggcgctcctc cgacgccgag gcgccccacg ggccccgga    4440
cgacggcggc gcgggcggga agggcggcag cctgccccgc agtgcgacac ccgggccccc    4500
cggagagcac ctggtgaatg gccggatgga ctttgccttc ccgggcagca ccaactccct    4560
gcacaggatg accacgacca gtgctgctgc ctatggcacc cacctgagcc acacgtgcc    4620
ccaccgcgtg ctaagcacat cctccaccct cacacgggac tacaactcac tgacccgctc    4680
agaacactca cactcgacca cactgcccag ggactactcc accctcacct ccgtctcctc    4740
ccacgactct cgcctgactg ctggtgtgcc cgacacgccc accgctgg tgttctctgc    4800
cctggggccc acatctctca gagtgagctg gcaggagccg cggtgcgagc ggccgctgca    4860
gggctacagt gtggagtacc agctgctgaa cggcggtgag ctgcatcggc tcaacatccc    4920
caaccctgcc cagacctcgg tggtggtgga agacctcctg cccaaccact cctacgtgtt    4980
ccgcgtgcgg gcccagagcc aggaaggctg gggccgagag cgtgagggtg tcatcaccat    5040
tgaatcccag gtgcacccgc agagcccact gtgtccctg ccaggctccg ccttcacttt    5100
gagcactccc agtgccccag gccgctggt gttcactgcc ctgagcccag actcgctgca    5160
gctgagctgg gagcggccac ggaggcccaa tggggatatc gtcggctacc tggtgacctg    5220
```

-continued

```
tgagatggcc caaggaggag ggccagccac cgcattccgg gtggatggag acagccccga    5280
gagccggctg accgtgccgg gcctcagcga aacgtgccc tacaagttca aggtgcaggc    5340
caggaccact gagggcttcg ggccagagcg cagggcatc atcaccatag agtcccagga    5400
tggaggaccc ttcccgcagc tgggcagccg tgccgggctc ttccagcacc cgctgcaaag    5460
cgagtacagc agcatcacca ccacccacac cagcgccacc gagcccttcc tagtggatgg    5520
gctgaccctg ggggcccagc acctggaggc aggcggctcc ctcacccggc atgtgaccca    5580
ggagtttgtg agccggacac tgaccaccag cggaaccctt agcacccaca tggaccaaca    5640
gttcttccaa acttgaccgc accctgcccc accccgcca cgtcccacta ggcgtcctcc    5700
cgactcctct cccggagcct cctcagctac tccatccttg cacccctggg ggcccagccc    5760
acccgcatgc acagagcagg ggctaggtgt ctcctgggag gcatgaaggg ggcaaggtcc    5820
gtcctctgtg ggcccaaacc tatttgtaac caaagagctg ggagcagcac aaggacccag    5880
cctttgttct gcacttaata aatggttttg ctactgctaa aaaaa                   5925

<210> SEQ ID NO 29
<211> LENGTH: 17
<212> TYPE: DNA
<213> ORGANISM: Artificial
<220> FEATURE:
<223> OTHER INFORMATION: primer for amplification of ITGB4

<400> SEQUENCE: 29
tgagccagct gagacca                                                     17

<210> SEQ ID NO 30
<211> LENGTH: 20
<212> TYPE: DNA
<213> ORGANISM: Artificial
<220> FEATURE:
<223> OTHER INFORMATION: primer for amplification of ITGB4

<400> SEQUENCE: 30
ctgggactcc cgaagttctc                                                  20
```

MARKERS FOR THE DIAGNOSIS OF LUNG CANCER

TECHNICAL FIELD

The present invention relates to a diagnostic marker specific for lung cancer. Also, the present invention relates to a composition and a kit, comprising an agent measuring the presence of the marker, and a method of diagnosing lung cancer using the composition or kit.

BACKGROUND ART

Lung cancer is a leading cause of cancer death worldwide. Lung cancer is responsible for about one-sixth of all cancer deaths. There are two major types of lung cancer: small cell lung cancer and non-small cell lung cancer. Non-small cell lung cancer is the representative lung cancer, which accounts for about 80% of all lung cancer. Adenocarcinoma, squamous cell carcinoma and large cell carcinoma are three types of non-small cell lung cancer. Since there are differences in histological properties as well as prognosis and therapy according to the type of lung cancer, accurate diagnosis is important. Despite the recent advances in cancer therapy, ten-year survival rates of patients with non-small cell lung cancer are 10% or even less. This is because non-small cell lung cancer is generally difficult to diagnose until the disease is relatively advanced. Under present situations, early diagnosis is the most effective method for increasing survival rates of the patients.

A variety of attempts have been made to diagnose lung cancer using markers. Some research reported diagnostic markers of lung cancer through expression of a limited number of target genes and proteins (Hibi et al., Am. J. Pathol. 1999, 155: 711-715; Brechot et al. Eur. J. Cancer 1997, 33: 385-391; Pastor et al., Eur. Respir. J. 1997, 10: 603-609; Morita et al., Int. J. Cancer 1998, 78: 286-292). Also, some reports described the finding of lung cancer marker genes using microarray techniques (Oncogene19_1519; Oncogene23_7734; Oncogene21_7749). However, there is no report involving the possibility of early diagnosis of lung cancer using the presently identified diagnostic markers of lung cancer.

Based on this background, the present inventors, in order to develop biomarkers capable of simply and accurately diagnosing lung cancer, performed primary screening for genes overexpressed only in lung cancer using a DNA chip, and identified highly significant markers by performing RT-PCR. As a result, PKP1, ABCC5, KRT15, KRT14, TRIM29, SERPINB5, TK1, GPX2, MMP1 and ITGB4 genes were identified. When the genes were practically applied to lung cancer samples, they were found to accurately diagnose lung cancer, thereby leading to the present invention.

DISCLOSURE OF THE INVENTION

It is therefore an object of the present invention to provide a diagnostic marker of lung cancer, which is at least one selected from among PKP1 (plakophilin 1), ABCC5 (ATP-binding cassette, subfamily C (CFTR/MRP), member 5), KRT15 (keratin 15), KRT14 (keratin 14), TRIM29 (tripartite motif-containing 29), SERPINB5 (serine (or cysteine) proteinase inhibitor, clade B (ovalbumin), member 5), TK1 (thymidine kinase 1, soluble), GPX2 (glutathione peroxidase 2), MMP1 (matrix metalloproteinase 1) and ITGB4 (integrin, beta 4).

It is another object of the present invention to provide a kit for detecting a diagnostic marker of lung cancer, comprising an agent measuring mRNA or protein levels of one or more genes selected from among PKP1, ABCC5, KRT15, KRT14, TRIM29, SERPINB5, TK1, GPX2, MMP1 and ITGB4.

It is a further object of the present invention to provide a composition for detecting a diagnostic marker of lung cancer, comprising a pair of primers specific for one or more genes selected from among PKP1, ABCC5, KRT15, KRT14, TRIM29, SERPINB5, TK1, GPX2, MMP1 and ITGB4.

It is yet another object of the present invention to provide a composition for detecting a diagnostic marker of lung cancer, comprising an antibody specific for one or more proteins selected from among PKP1, ABCC5, KRT15, KRT14, TRIM29, SERPINB5, TK1, GPX2, MMP1 and ITGB4.

It is still another object of the present invention to provide a method of diagnosing lung cancer using primers specific for one or more genes selected from among PKP1, ABCC5, KRT15, KRT14, TRIM29, SERPINB5, TK1, GPX2, MMP1 and ITGB4.

It is still another object of the present invention to provide a method of diagnosing lung cancer using an antibody specific for one or more proteins selected from among PKP1, ABCC5, KRT15, KRT14, TRIM29, SERPINB5, TK1, GPX2, MMP1 and ITGB4.

BEST MODE FOR CARRYING OUT THE INVENTION

Figure 1:
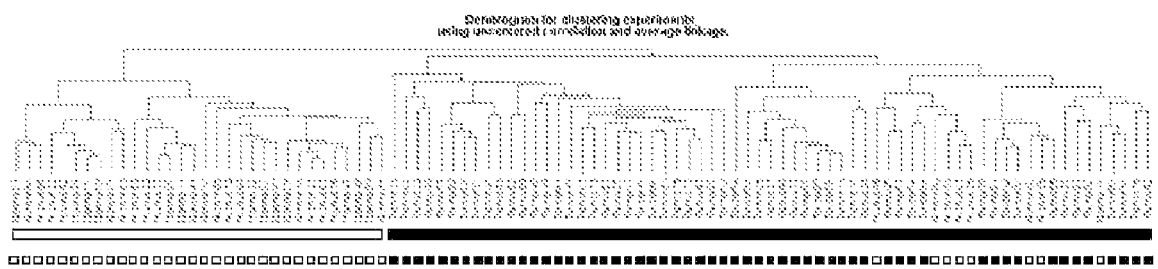
FIG. 1 shows the clustering of 57 tumorous and 40 normal lung tissues using gene expression data. Tumorous lung tissues are represented by "Tumor (black rectangular shape)", and normal lung tissues are represented by "Normal (white rectangular shape)". The left white bar indicates a group in which most of the normal lung tissues cluster together, and the right black bar indicates another group in which the tumor lung tissues cluster together.

In one aspect, the present invention relates to a lung cancer diagnostic marker selected from PKP1, ABCC5, KRT15, KRT14, TRIM29, SERPINB5, TK1, GPX2, MMP1 and ITGB4.

The term "diagnosis", as used herein, refers to evaluation of the presence or properties of pathological states. With respect to the objects of the present invention, the diagnosis is to determine the incidence of lung cancer.

The term "lung cancer", as used herein, refers to malignant tumor occurring in the lung, and includes both small cell lung cancer and non-small cell lung cancer including adenocarcinoma, squamous cell carcinoma and large cell carcinoma.

The term "marker for diagnosing, marker for diagnosis or diagnostic marker", as used herein, is intended to indicate a substance capable of diagnosing lung cancer by distinguishing lung cancer cells from normal cells, and includes organic biological molecules, quantities of which are increased or decreased in lung cancer cells relative to normal cells, such as polypeptides or nucleic acids (e.g., mRNA, etc.), lipids, glycolipids, glycoproteins and sugars (monosaccharides, disaccharides, oligosaccharides, etc.). With respect to the objects of the present invention, lung cancer diagnostic markers are PKP1, ABCC5, KRT15, KRT14, TRIM29, SERPINB5, TK1, GPX2, MMP1 and ITGB4, which are genes whose expression is increased in lung cancer cells.

The selection and application of significant diagnostic markers determine the reliability of diagnosis results. A significant diagnostic marker means a marker that has high validity, giving accurate diagnosis results, and high reliability, supplying constant results upon repeated measurement. The lung cancer diagnostic markers of the present invention, which are genes whose expression always increases by direct or indirect factors when lung cancer occurs, display the same results upon repeated tests, and have high reliability due to a great difference in expression levels compared to a control, thus having a very low possibility of giving false results. Therefore, diagnosis based on the results obtained by measuring the expression levels of the significant diagnostic markers of the present invention is valid and reliable.

The PKP1, ABCC5, KRT15, KRT14, TRIM29, SERPINB5, TK1, GPX2, MMP1 and ITGB4 genes of the present invention may be used as diagnostic markers of lung cancer because they are expressed at high levels specifically in lung cancer cells compared to cells of normal lung tissue.

All of the genes are useful as diagnostic markers of lung cancer. However, with respect to the present object of providing rapid, simple and accurate markers, it is preferable to detect a limited number of markers make a medical decision. This is economical in terms of preventing waste of time and resources. Since PKP1 and ABCC5 are expressed specifically in lung cancer cells, they have very high reliability allowing diagnosis of lung cancer even when used alone. Therefore, the diagnosis of lung cancer is preferably carried out using either PKP1 or ABCC5 alone, or both of them, as markers.

In addition, the diagnosis of lung cancer may be carried out using one to eight genes selected from among KRT15, KRT14, TRIM29, SERPINB5, TK1, GPX2, MMP1 and ITGB4, as markers.

Herein, genes expressed at almost the same levels in cells of normal lung tissue and lung cancer cells, for example, DCK (deoxycytidine kinase) and SEP15 (selenoprotein, 15-KD), may be used as quantitative controls.

In another aspect, the present invention relates to a kit for detecting a diagnostic marker of lung cancer, comprising an agent measuring mRNA or protein levels of one or two genes selected from PKP1 and ABCC5.

The kit may further include an agent measuring mRNA or protein levels of one to eight genes selected from among KRT15, KRT14, TRIM29, SERPINB5, TK1, GPX2, MMP1 and ITGB4.

Gene expression levels of biological samples may be determined by measuring mRNA or protein levels.

The term "measurement of mRNA expression levels", as used herein, is a process of assessing the presence and expression levels of mRNA of lung cancer marker genes in biological samples for diagnosing lung cancer, in which the amount of mRNA is measured. Analysis methods for measuring mRNA levels include, but are not limited to, RT-PCR, competitive RT-PCR, real-time RT-PCR, RNase protection assay (RPA), Northern blotting and DNA chip assay.

The "measurement of protein expression levels", as used herein, is a process of assessing the presence and expression levels of proteins expressed from lung cancer marker genes in biological samples for diagnosing lung cancer, in which the amount of protein products of the marker genes is measured using antibodies specifically binding to the proteins. Analysis methods for measuring protein levels include, but are not limited to, Western blotting, enzyme linked immunosorbent assay (ELISA), radioimmunoassay (RIA), radioimmunodiffusion, ouchterlony immunodiffusion, rocket immunoelectrophoresis, immunohistostaining, immunoprecipitation assay, complement fixation assay, FACS, and protein chip assay.

The detection kit of the present invention is composed of a composition, solution or apparatus, which includes one or more kinds of different constituents suitable for analysis methods.

Preferably, the present invention relates to a kit for detecting a diagnostic marker, which is characterized by including essential elements required for performing RT-PCR. An RT-PCR kit includes a pair of primers specific for each marker gene. The primers are nucleotides having sequences specific to a nucleic acid sequence of each marker gene, and are about 7 bp to 50 bp in length, more preferably about 10 bp to 30 bp in length. Also, the RT-PCR kit may include primers specific to a nucleic acid sequence of a control gene. The RT-PCR may further include test tubes or other suitable containers, reaction buffers (varying in pH and magnesium concentrations), deoxynucleotides (dNTPs), enzymes such as Taq-polymerase and reverse transcriptase, DNAse, RNAse inhibitor, DEPC-treated water, and sterile water.

In addition, preferably, the present invention relates to a diagnostic kit, which is characterized by including essential elements required for performing a DNA chip assay. A DNA chip kit may include a base plate onto which genes or fragments thereof, cDNA or oligonucleotides, are attached, and reagents, agents and enzymes for preparing fluorescent probes. Also, the base plate may include a control gene or fragments thereof, such as cDNA or oligonucleotides.

Further, preferably, the present invention relates to a diagnostic kit, which is characterized by including essential elements required for performing ELISA. An ELISA kit includes antibodies specific to marker proteins. The antibodies are monoclonal, polyclonal or recombinant antibodies, which have high specificity and affinity to each marker protein and rarely have cross-reactivity to other proteins. Also, the ELISA kit may include an antibody specific to a control protein. The ELISA kit may further include reagents capable of detecting bound antibodies, for example, a labeled secondary antibody, chromophores, enzymes (e.g., conjugated with an antibody) and their substrates, or other substances capable of binding to the antibodies.

An RT-PCR kit for detecting lung cancer markers includes a pair of primers specific to one to two genes selected from PKP1 and ABCC5. Also, the RT-PCR kit may include a pair of primers specific to one to eight genes selected from among KRT15, KRT14, TRIM29, SERPINB5, TK1, GPX2, MMP1 and ITGB4 genes.

A DNA chip kit for detecting lung cancer markers includes a base plate onto which cDNA corresponding to one to two genes selected from PKP1 and ABCC5, or fragments thereof, is attached. Also, cDNA corresponding to one to eight genes selected from among KRT15, KRT14, TRIM29, SERPINB5, TK1, GPX2, MMP1 and ITGB4 genes, or fragments thereof, may be attached and immobilized onto a base plate.

An ELISA kit for detecting lung cancer markers includes an antibody specific to one or two proteins selected from PKP1 and ABCC5. Also, the ELISA kit may include an antibody specific to one to eight genes selected from among KRT15, KRT14, TRIM29, SERPINB5, TK1, GPX2, MMP1 and ITGB4.

In a further aspect, the present invention relates to a composition for detecting a diagnostic marker of lung cancer, comprising primers specific to one or two genes selected from PKP1 and ABCC5.

The above composition may further include primers specific to one to eight genes selected from among KRT15, KRT14, TRIM29, SERPINB5, TK1, GPX2, MMP1 and ITGB4.

As used herein, "primer" means a short nucleic acid sequence having a free 3' hydroxyl group, which is able to form base-pairing interaction with a complementary template and serves as a starting point for replication of the template strand. A primer is able to initiate DNA synthesis in the presence of a reagent for polymerization (i.e., DNA polymerase or reverse transcriptase) and four different nucleosides triphosphates at suitable buffers and temperature. The primers of the present invention, specific to each of the marker genes, are sense and antisense nucleic acids having a sequence of 7 to 50 nucleotides. The primer may have additional properties that do not change the nature of the primer to serve as a starting point for DNA synthesis.

The primers of the present invention may be chemically synthesized using a phosphoramidite solid support method or other widely known methods. These nucleic acid sequences may also be modified using many means known in the art. Non-limiting examples of such modifications include methylation, capsulation, replacement of one or more native nucleotides with analogues thereof, and inter-nucleotide modifications, for example, modifications to uncharged conjugates (e.g., methyl phosphonate, phosphotriester, phosphoroamidate, carbamate, etc.) or charged conjugates (e.g., phosphorothioate, phosphorodithioate, etc.). Nucleic acids may contain one or more additionally covalent-bonded residues, which are exemplified by proteins (e.g., nucleases, toxins, antibodies, signal peptides, poly-L-lysine, etc.), intercalating agents (e.g., acridine, psoralene, etc.), chelating agents (e.g., metals, radioactive metals, iron, oxidative metals, etc.), and alkylating agents. The nucleic acid sequences of the present invention may also be altered using a label capable of directly or indirectly supplying a detectable signal. Examples of the label include radioisotopes, fluorescent molecules and biotin.

The composition for detecting a diagnostic marker of lung cancer includes a pair of primers specific to one to two genes selected from PKP1 and ABCC5. Primers for amplifying PKP1 (SEQ ID NO. 1) are preferably represented by SEQ ID NOS. 2 and 3, and primers for amplifying ABCC5 (SEQ ID NO. 4) are preferably represented by SEQ ID NOS. 5 and 6. Also, the composition may further include a pair of primers specific to one to eight genes selected from among KRT15, KRT14, TRIM29, SERPINB5, TK1, GPX2, MMP1 and ITGB4 genes. Primers for amplifying KRT15 (SEQ ID NO. 7) are preferably represented by SEQ ID NOS. 8 and 9. Primers for amplifying KRT14 (SEQ ID NO. 10) are preferably represented by SEQ ID NOS. 11 and 12. Primers for amplifying TRIM29 (SEQ ID NO. 13) are preferably represented by SEQ ID NOS. 14 and 15. Primers for amplifying SERPINB5 (SEQ ID NO. 16) are preferably represented by SEQ ID NOS. 17 and 18. Primers for amplifying TK1 (SEQ ID NO. 19) are preferably represented by SEQ ID NOS. 20 and 21. Primers for amplifying GPX2 (SEQ ID NO. 22) are preferably represented by SEQ ID NOS. 23 and 24. Primers for amplifying MMP1 (SEQ ID NO. 25) are preferably represented by SEQ ID NOS. 26 and 27. Primers for amplifying ITGB4 (SEQ ID NO. 28) are preferably represented by SEQ ID NOS. 29 and 30.

In yet another aspect, the present invention relates to a composition for detecting a diagnostic marker of lung cancer, comprising an antibody specific to one or two proteins selected from PKP1 and ABCC5.

The above composition may further include an antibody specific to one to eight proteins selected from among KRT15, KRT14, TRIM29, SERPINB5, TK1, GPX2, MMP1 and ITGB4.

The term "antibody", as used herein, refers to a specific protein molecule that indicates an antigenic region. With respect to the objects of the present invention, an antibody binds specifically to a marker protein, and includes all of polyclonal antibodies, monoclonal antibodies and recombinant antibodies.

Antibody production using the lung cancer marker proteins identified as described above may be easily carried out using techniques widely known in the art.

Polyclonal antibodies may be produced by a method widely known in the art, which includes injecting the lung cancer marker protein antigen into an animal and collecting blood samples from the animal to obtain serum containing antibodies. Such polyclonal antibodies may be prepared from a certain animal host, such as goats, rabbits, sheep, monkeys, horses, pigs, cows and dogs.

Monoclonal antibodies may be prepared by a method widely known in the art, such as a hybridoma method (see, Kohler and Milstein (1976) European Journal of Immunology 6:511-519), or a phage antibody library technique (Clackson et al., Nature, 352:624-628, 1991; Marks et al, J. Mol. Biol., 222:58, 1-597, 1991).

The hybridoma method employs cells from an immunologically suitable host animal injected with a diagnostic marker protein of lung cancer as an antigen, such as mice, and a cancer or myeloma cell line as another group. Cells of the two groups are fused with each other by a method widely known in the art, for example, using polyethylene glycol, and antibody-producing cells are proliferated by a standard tissue culture method. After uniform cell colonies are obtained by subcloning using a limited dilution technique, hybridomas capable of producing an antibody specific for the diagnostic marker protein of lung cancer are cultivated in large scale in vitro or in vivo according to a standard technique. Monoclonal antibodies produced by the hybridomas may be used in an unpurified form, but are preferably used after being highly purified by a method widely known in the art so as to obtain best results.

The phage antibody library method includes constructing a phage antibody library in vitro by obtaining genes for antibodies (single-chain fragment variable (scFv)) to a variety of intracellular lung cancer markers and expressing them in a fusion protein form on the surface of phages, and isolating monoclonal antibodies binding to lung cancer-specific proteins from the library.

Antibodies prepared by the above methods are isolated using gel electrophoresis, dialysis, salting out, ion exchange chromatography, affinity chromatography, and the like.

In addition, the antibodies of the present invention include complete forms having two full-length light chains and two full-length heavy chains, as well as functional fragments of antibody molecules. The functional fragments of antibody molecules refer to fragments retaining at least an antigen-binding function, and include Fab, F(ab'), F(ab')2, Fv and the like.

The composition for detecting a lung cancer marker includes an antibody specific for one to two proteins selected from PKP1 and ABCC5. Also, the composition may further include an antibody specific to one to eight proteins selected from among KRT15, KRT14, TRIM29, SERPINB5, TK1, GPX2, MMP1 and ITGB4.

In still another aspect, the present invention relates to a method of diagnosing lung cancer, comprising measuring mRNA levels in a biological sample from a patient with suspected lung cancer using primers specific to one or two genes selected from PKP1 and ABCC5, and comparing mRNA levels of the sample from the patient with those of a normal control sample to determine an increase in mRNA levels.

The above method may further include diagnosing lung cancer using primers specific to one to eight genes selected from among KRT15, KRT14, TRIM29, SERPINB5, TK1, GPX2, MMP1 and ITGB4.

The isolation of mRNA from a biological sample may be achieved using a known process, and mRNA levels may be measured by a variety of methods.

The term "biological sample", as used herein, includes, but is not limited to, samples displaying a difference in expression levels of a lung cancer marker gene, such as tissues, cells, whole blood, serum, plasma, saliva, sputum, cerebrospinal fluid or urine.

Analysis methods for measuring mRNA levels include, but are not limited to, RT-PCR, competitive RT-PCR, real-time RT-PCR, RNase protection assay (RPA), Northern blotting and DNA chip assay.

With the detection methods, a patient with suspected lung cancer is compared with a normal control for mRNA expression levels of a lung cancer marker gene, and the patient's suspected lung cancer is diagnosed by determining whether expression levels of mRNA from the lung cancer marker gene have significantly increased.

mRNA expression levels are preferably measured by RT-PCR using primers specific to a gene as a lung cancer marker.

RT-PCR is a method that was introduced to analyze RNA by P. Seeburg (Cold Spring Harb Symp Quant Biol 1986, Pt 1:669-677), with which cDNA is synthesized from mRNA by reverse transcription and amplified by PCR. At the amplification step, a pair of primers prepared in a fashion specific to a diagnostic marker of lung cancer is used. RT-PCR products are electrophoresed, and patterns and thicknesses of bands are analyzed to determine the expression and levels of mRNA from a gene used as a diagnostic marker of lung cancer while comparing the mRNA expression and levels with those of a control, thereby simply diagnosing the incidence of lung cancer.

Alternatively, mRNA expression levels are measured using a DNA chip in which the lung cancer marker genes or nucleic acid fragments thereof are anchored at high density to a glass-like base plate. A cDNA probe labeled with a fluorescent substance at its end or internal region is prepared using mRNA isolated from a sample, and is hybridized with the DNA chip. The DNA chip is then read to determine the presence or expression levels of the gene, thereby diagnosing the incidence of lung cancer.

In still another aspect, the present invention relates to a method of diagnosing lung cancer, comprising measuring protein levels by contacting an antibody specific to one or two genes selected from PKP1 and ABCC5 with a biological sample from a patient with suspected lung cancer to form antigen-antibody complexes, and comparing protein levels of the sample from the patient with those of a normal control sample to determine an increase in protein levels.

The above method may further include diagnosing lung cancer using an antibody specific to one to eight proteins selected from among KRT15, KRT14, TRIM29, SERPINB5, TK1, GPX2, MMP1 and ITGB4.

The isolation of proteins from a biological sample may be achieved using a known process, and protein levels may be measured by a variety of methods.

Analysis methods for measuring protein levels include, but are not limited to, Western blotting, ELISA, radioimmunoassay (RIA), radioimmunodiffusion, ouchterlony immunodiffusion, rocket immunoelectrophoresis, immunohistostaining, immunoprecipitation assay, complement fixation assay, FACS, and protein chip assay.

With the analysis methods, a patient with suspected lung cancer is compared with a normal control for the amount of formed antigen-antibody complexes, and the patient's suspected lung cancer is diagnosed by evaluating a significant increase in expression levels of a protein from the lung cancer marker gene.

The term "antigen-antibody complexes", as used herein, refers to binding products of a lung cancer marker protein to an antibody specific thereto. The amount of formed antigen-antibody complexes may be quantitatively determined by measuring the signal size of a detection label.

Such a detection label may be selected from the group consisting of enzymes, fluorescent substances, ligands, luminescent substances, microparticles, redox molecules and radioactive isotopes, but the present invention is not limited to the examples. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphenolpyruvate decarboxylase, and β-latamase. Examples of the fluorescent substances include, but are not limited to, fluorescin, isothiocyanate, rhodamine, phycoerythrin, phycocyanin, allophycocyanin, o-phthaldehyde and fluorescamin. Examples of the ligands include, but are not limited to, biotin derivatives. Examples of luminescent substances include, but are not limited to, acridinium esters, luciferin and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, K4W(CN)$_8$, [Os(bpy)$_3$]$^{2+}$, [RU(bpy)$_3$]$^{2+}$ and [MO(CN)$_8$]$^{4-}$. Examples of the radioactive isotopes include, but are not limited to, $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I and $^{186}$Re.

Preferably, the protein expression levels are measured by ELISA. Examples of ELISA include direct ELISA using a labeled antibody recognizing an antigen immobilized on a solid support; indirect ELISA using a labeled antibody recognizing a capture antibody forming complexes with an antigen immobilized on a solid support; direct sandwich ELISA using a labeled antibody recognizing an antigen bound to a antibody immobilized on a solid support; and indirect sandwich ELISA, in which a captured antigen bound to an antibody immobilized on a solid support is detected by first adding an antigen-specific antibody, and then a secondary labeled antibody which binds the antigen-specific antibody. More preferably, the protein expression levels are detected by sandwich ELISA, where a sample reacts with an antibody immobilized on a solid support, and the resulting antigen-antibody complexes are detected by adding a labeled antibody specific for the antigen, followed by enzymatic development, or by first adding an antigen-specific antibody and then a secondary labeled antibody which binds to the antigen-specific antibody, followed by enzymatic development. The incidence of lung cancer may be diagnosed by measuring the degree of complex formation of a lung cancer marker protein and an antibody thereto.

In addition, the protein expression levels are preferably measured using a protein chip in which one or more antibodies to the lung cancer markers are arrayed and immobilized at predetermined positions of a base plate at high density. By a method of analyzing a sample using a protein chip, proteins are isolated from the sample and hybridized with the protein chip to form antigen-antibody complexes. The protein chip is then read to determine the presence or expression levels of the proteins, thereby diagnosing the incidence of lung cancer.

Further, the measurement of protein expression levels is preferably achieved using Western blotting using one or more antibodies to the lung cancer makers. Total proteins are isolated from a sample, electrophoresed to be separated according to size, transferred onto a nitrocellulose membrane, and reacted with an antibody. The amount of proteins produced by gene expression is determined by measuring the amount of antigen-antibody complexes produced using a labeled antibody, thereby diagnosing the incidence of lung cancer.

The detection methods are composed of methods of assessing expression levels of maker genes in a control and cells in which lung cancer occurs. mRNA or protein levels may be expressed as an absolute (e.g., μg/ml) or relative (e.g., relative intensity of signals) difference in the amount of marker proteins.

A better understanding of the present invention may be obtained through the following examples which are set forth to illustrate, but are not to be construed as the limit of the present invention.

Example 1

Analysis of Gene Expression in Squamous Cell Carcinoma Cells of the Lung and Normal Lung Tissue <1-1> RNA Isolation from Patient Specimens Patient specimens were obtained from Korean Cancer Center Hospital. RNA was isolated from the specimens from patients with squamous cell carcinoma of the lung using a TriZol reagent (InVitrogen) according to the manufacturer's protocol. 10 ml of the TriZol reagent was used per patient specimen, which was cut into a size of 1 cm$^3$. The concentration of the isolated RNA was determined using a spectrophotometer.

<1-2> Microarray Analysis

The gene expression patterns of the patient specimens were assessed using an 8K human cDNA microarray (GenePlorer™ TwinChip™ human-8K set1), which was purchased from Digital Genomics Inc., Korea. The microarray contained 8,170 different cDNA probes that were repeated twice, and the related information is available from a web site, http://annotation.digital-genomics.co.kr/excel/human8 2kset1.xls. To compare 97 samples with each other for gene expression patterns, the gene expression of each specimen was compared with that of a common reference sample. The common reference sample was prepared by mixing the equal amounts of RNA isolated from eight lung-derived cell lines. Cell lines used were NCI-H23, NCI-H1299, NCI-H596, A-549, NCI-H358, NCI-H128, SK-LU-1, and Malme-3M.

Samples for hybridization were prepared as follows. 20 μg of RNA was reverse transcribed in the presence of aminoallyl-modified dUTP and coupled to a fluorescent dye by a chemical method. Samples extracted from lung cancer patients were labeled with a Cy5 fluorescent dye, and the common reference sample RNA was labeled with a Cy3 fluorescent dye. The two samples labeled with two different fluorescent dyes were mixed and hybridized to the microarray. Then, the DNA chip was washed with a washing solution containing SSC to eliminate non-specific hybridizations. The washed DNA chip was scanned using a confocal laser scanner (Perkin Elmer, Scanarray Lite), and the obtained fluorescent data present at each spot were saved as TIFF images. The TIFF images were quantified with GenePix 3.0 (Axon Instruments) to quantify the fluorescence intensity at each spot. Quantitative results obtained from GenePix 3.0 were normalized using the 'lowess' function supplied by the S-plus statistical package (InSightful) according to a method suggested by Yang et al. (Nucleic Acids Res 2002, 30:e15).

<1-3> Overall Evaluation of Microarray Results Data

Figure 2:
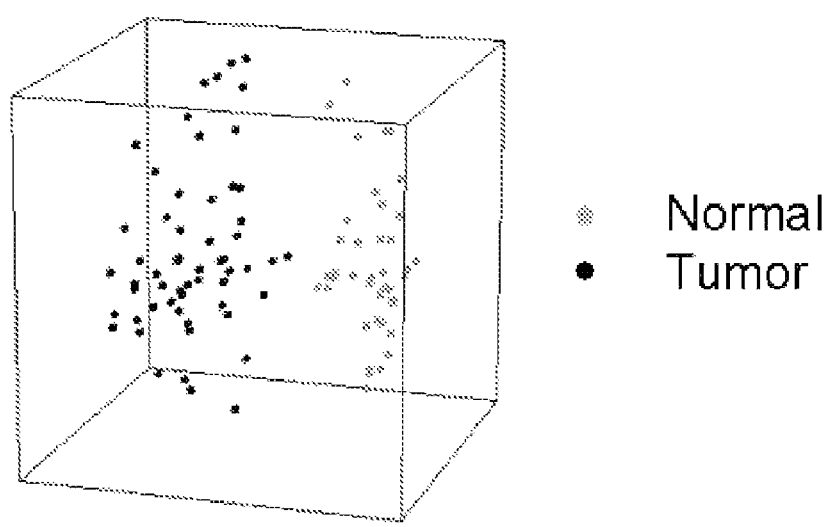
FIG. 2 shows a 3-D visualization of gene expression patterns by multidimensional scaling. The black circle indicates tumorous lung tissues, and the gray circle indicates normal lung tissues. Spots placed near each other in three dimensional space indicate that they have similar gene expression patterns. Tumorous lung tissues form one cluster, and normal lung tissues form another cluster, indicating that each of the tumorous and normal lung tissues has a specific gene expression pattern.

Gene expression patterns in squamous cell carcinomas of the lung and normal lung tissues were analyzed through analysis of the cDNA (complementary DNA) microarray, which contained over 8,000 probes. The whole gene expression patterns of squamous cell carcinomas of the lung were evaluated using clustering analysis and multidimensional scaling. Clustering analysis revealed that the squamous cell carcinoma and normal lung tissues were separated into two large distinct clusters (FIG. 1). Multidimensional scaling confirmed the obvious difference between the squamous cell carcinoma and normal lung tissues in gene expression patterns (FIG. 2). These results indicate that gene expression results obtained through microarray analysis are useful data for selection of marker genes capable of diagnosing squamous cell carcinoma of the lung.

Example 2

Selection of Genes Expressed at Different Levels in Non-Small Cell Lung Cancer and Normal Lung Tissue <2-1> Gene Selection by T-Test A t-test was conducted in a significance level of $p=10^{-6}$ so as to select genes whose expression is significantly different between squamous cell carcinoma and normal lung tissues. Since gene selection in the significance level is expected to generate only one false-positive gene in one million tests, all genes thus selected are genes practically different in expression levels. The gene selection by the t-test resulted in the selection of 832 genes exhibiting a significant difference in expression levels. Among the selected genes, 319 genes were expressed at higher levels in squamous cell carcinoma lung tissues, and 513 genes were expressed at higher levels in normal lung tissues. Since genes displaying high-level expression in tumorous lung tissues are required for diagnosing lung cancer, diagnostic markers were selected from among the 319 genes highly expressed in lung cancer.

<2-2> Identification of Diagnostic Markers Using RT-PCR

Expression levels of the selected genes were estimated by RT-PCR in order to identify genes highly useful as diagnostic markers for the early diagnosis of lung cancer. For RT-PCR, tumorous lung tissues were collected from eight patients with squamous cell carcinoma of the lung, and normal tissues were also prepared. RT-PCR was carried out as follows. 5 μg of RNA was reverse transcribed in a 20 μl reaction volume, and was diluted with distilled water to 100 μl. Using 2 μl of the diluted RT-PCR product as a template, a 25-cycle PCR was carried out with a pair of primers specific to each gene in a 25-μl reaction volume. 8 μl of the PCR product was electrophoresed on a 2% agarose gel containing 0.5 μg/ml of EtBr, and DNA bands were visualized under UV light.

Among the 319 genes highly expressed in squamous cell carcinoma of the lung, 39 genes exerting a two-fold difference in expression levels were selected (Table 1), and gene expression levels were confirmed by RT-PCR.

TABLE 1

Genes expressed in tumorous lung tissues more than twice as high as in normal tissues among the genes selected by the t-test

| Serial No. | Difference in expression levels (lung cancer/normal) | Gene name | GenBank Accession number | UniGen cluster ID | Gene Symbol |
|---|---|---|---|---|---|
| 1 | 13 | keratin 15 | X07696 | Hs. 80342 | KRT15 |
| 2 | 9.2 | keratin 14 (epidermolysis bullosa simplex, Dowling-Meara, Koebner) | NM_000526 | Hs. 355214 | KRT14 |
| 3 | 7 | tripartite motif-containing 29 | AA131550 | Hs. 82237 | TRIM29 |
| 4 | 6.8 | ubiquitin carboxyl-terminal esterase L1 (ubiquitin thiolesterase) | AI928978 | Hs. 76118 | UCHL1 |
| 5 | 4.7 | cystatin A (stefin A) | AI680589 | Hs. 412999 | CSTA |
| 6 | 4.2 | serine (or cysteine) proteinase inhibitor, clade B (ovalbumin), member 5 | AI435384 | Hs. 55279 | SERPINB5 |
| 7 | 3.6 | BarH-like homeobox 2 | AJ243512 | Hs. 167218 | BARX2 |
| 8 | 3.5 | collagen, type I, alpha 1 | K01228 | Hs. 172928 | COL1A1 |
| 9 | 3.3 | small proline-rich protein 1B (cornifin) | M19888 | Hs. 1076 | SPRR1B |
| 10 | 3.2 | plakophilin 1 (ectodermal dysplasia/skin fragility syndrome) | Z34974 | Hs. 313068 | PKP1 |
| 11 | 3.2 | thymidine kinase 1, soluble | K02581 | Hs. 164457 | TK1 |
| 12 | 3.1 | follistatin | NM_013409 | Hs. 9914 | FST |
| 13 | 2.6 | Kruppel-like factor 5 (intestinal) | D14520 | Hs. 84728 | KLF5 |
| 14 | 2.6 | eukaryotic translation initiation factor 1A, Y-linked | AF000987 | Hs. 461178 | EIF1AY |
| 15 | 2.5 | Similar to My016 protein (LOC339088), mRNA | AA398908 | Hs. 449815 | |
| 16 | 2.5 | ATP-binding cassette, sub-family C (CFTR/MRP), member 5 | AB005659 | Hs. 34744 | ABCC5 |
| 17 | 2.5 | desmocollin 2 | AI888282 | Hs. 95612 | DSC2 |
| 18 | 2.4 | non-metastatic cells 1, protein (NM23A) expressed therein | AW024667 | Hs. 118638 | NME1 |
| 19 | 2.4 | flap structure-specific endonuclease 1 | X76771 | Hs. 409065 | FEN1 |
| 20 | 2.4 | nuclear cap binding protein subunit 2, 20 kDa | AI955092 | Hs. 240770 | NCBP2 |
| 21 | 2.4 | histone 1, H2ae | AA436989 | Hs. 121017 | HIST1H2AE |
| 22 | 2.4 | procollagen-lysine, 2-oxoglutarate 5-dioxygenase (lysine hydroxylase) 2 | U84573 | Hs. 41270 | PLOD2 |
| 23 | 2.4 | protein kinase, cAMP-dependent, catalytic, alpha | X07767 | Hs. 194350 | PRKACA |
| 24 | 2.3 | vaccinia related kinase 1 | AA312869 | Hs. 422662 | VRK1 |
| 25 | 2.3 | neurotrophic tyrosine kinase, receptor, type 2 | U12140 | Hs. 439109 | NTRK2 |
| 26 | 2.3 | protein tyrosine phosphatase, receptor type, F | AI735029 | Hs. 75216 | PTPRF |
| 27 | 2.3 | asparagine synthetase | NM 001673 | Hs. 446546 | ASNS |
| 28 | 2.3 | jagged 1 (Alagille syndrome) | U61276 | Hs. 409202 | JAG1 |
| 29 | 2.2 | S-adenosylhomocysteine hydrolase | M61831 | Hs. 388004 | AHCY |
| 30 | 2.2 | FK506 binding protein 4, 59 kDa | M88279 | Hs. 848 | FKBP4 |
| 31 | 2.2 | glutathione peroxidase 2 (gastrointestinal) | X68314 | Hs. 2704 | GPX2 |
| 32 | 2.2 | matrix metalloproteinase 1 (interstitial collagenase) | M13509 | Hs. 83169 | MMP1 |
| 33 | 2.2 | integrin, beta 4 | X51841 | Hs. 85266 | ITGB4 |
| 34 | 2.1 | nipsnap homolog 1 (C. elegans) | AJ001258 | Hs. 173878 | NIPSNAP1 |

TABLE 1-continued

Genes expressed in tumorous lung tissues more than twice as high as in normal tissues among the genes selected by the t-test

| Serial No. | Difference in expression levels (lung cancer/normal) | Gene name | GenBank Accession number | UniGen cluster ID | Gene Symbol |
|---|---|---|---|---|---|
| 35 | 2.1 | solute carrier family 7, (cationic amino acid transporter, y+ system) member 11 | N35555 | Hs. 6682 | SLC7A11 |
| 36 | 2.1 | protein kinase, DNA-activated, catalytic polypeptide | U34994 | Hs. 415749 | PRKDC |
| 37 | 2.1 | tumor protein D52 | U18914 | Hs. 162089 | TPD52 |
| 38 | 2.1 | phosphatidic acid phosphatase type 2C | AF047760 | Hs. 24879 | PPAP2C |
| 39 | 2.1 | proteasome (prosome, macropain) 26S subunit, non-ATPase, 14 | U86782 | Hs. 178761 | PSMD14 |

Figure 3:
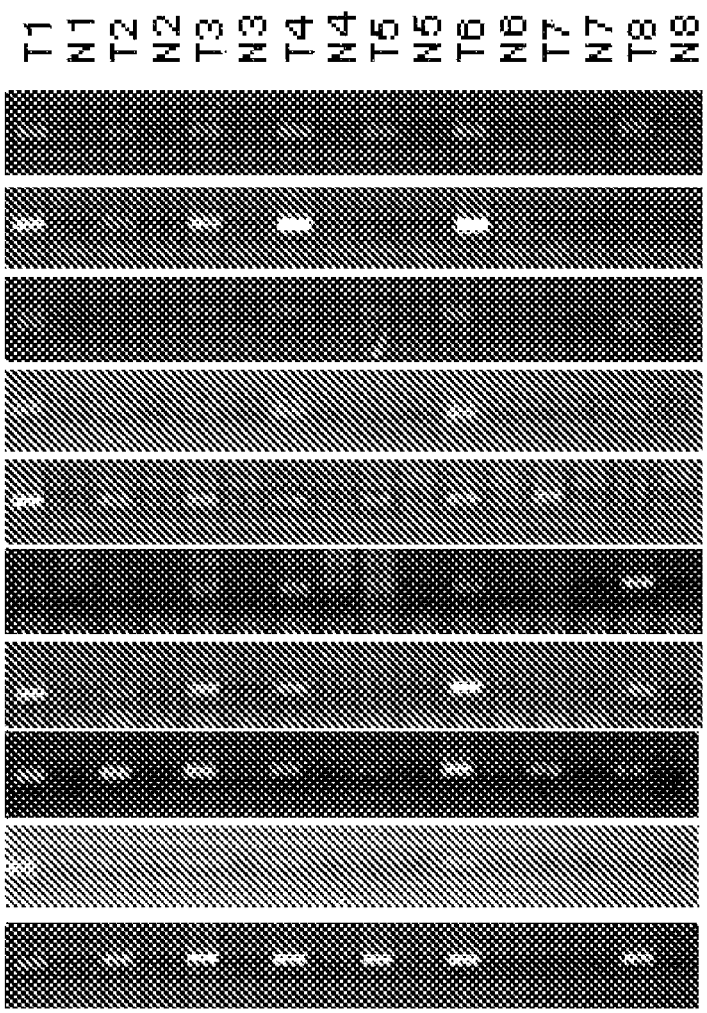
FIG. 3 shows the results of RT-PCR for confirming the difference in expression levels between tumorous and normal lung tissues. Ten genes are expressed not in normal lung tissues but in tumorous lung tissues.

Among the 39 selected genes, 10 genes were found to be expressed not in normal lung tissues but in tumorous lung tissues (FIG. 3). The rest 29 genes were expressed in tumorous lung tissues at higher levels than in normal tissues, and 10 genes did not display any difference in expression levels between tumorous and normal lung tissues. RT-PCR revealed that 39 of the 49 genes were expressed in tumorous lung tissues at higher levels than in normal tissues, indicating that 78% of the microarray results are consistent with the RT-PCR results. In particular, the 10 genes specifically expressed in tumorous lung tissues can be used as diagnostic markers for diagnosing lung cancer.

INDUSTRIAL APPLICABILITY

The lung cancer markers of the present invention allow the simple accurate diagnosis of lung cancer through detection of their mRNA or protein expression levels.

The invention claimed is:

1. A method of diagnosing lung cancer, comprising:
   measuring mRNA levels in a lung tissue sample from a patient with suspected lung cancer using primers specific for PKP1 and TRIM29 mRNAs; and
   comparing the mRNA levels of the sample from the patient with PKP1 and TRIM29 mRNA levels from a normal lung tissue control sample, wherein a higher level of PKP1 and TRIM29 mRNAs in the patient sample as compared to the control sample indicates that the patient has lung cancer.

2. The method according to claim 1, which further comprises using primers specific for one to eight mRNAs selected from ABCC5, KRT15, KRT14, SERPINB5, TK1, GPX2, MMP1, and ITGB4.

* * * * *